(12) United States Patent
Choo et al.

(10) Patent No.: US 6,746,838 B1
(45) Date of Patent: Jun. 8, 2004

(54) NUCLEIC ACID BINDING PROTEINS

(75) Inventors: Yen Choo, Cambridge (GB); Aaron Klug, Cambridge (GB); Mark Isalan, London (GB)

(73) Assignee: Gendaq Limited, London (GB)

( * ) Notice: Subject to any disclaimer, the term of this patent is extended or adjusted under 35 U.S.C. 154(b) by 0 days.

(21) Appl. No.: 09/424,487

(22) PCT Filed: May 26, 1998

(86) PCT No.: PCT/GB98/01512

§ 371 (c)(1),
(2), (4) Date: Feb. 29, 2000

(87) PCT Pub. No.: WO98/53058

PCT Pub. Date: Nov. 26, 1998

(30) Foreign Application Priority Data

May 23, 1997 (GB) .............................................. 9710809

(51) Int. Cl.[7] .............................................. C12Q 1/68
(52) U.S. Cl. ........................ 435/6; 435/7.1; 435/91.1; 536/23.1; 530/350
(58) Field of Search ........................ 435/7.1, 6, 91.1; 536/23.1; 530/350

(56) References Cited

U.S. PATENT DOCUMENTS

| | | | |
|---|---|---|---|
| 4,990,607 A | 2/1991 | Katagiri et al. ................. | 435/6 |
| 5,096,814 A | 3/1992 | Aivasidis et al. .............. | 435/6 |
| 5,096,815 A | 3/1992 | Ladner et al. .............. | 435/69.1 |
| 5,198,346 A | 3/1993 | Ladner et al. .............. | 435/69.1 |
| 5,223,409 A | 6/1993 | Ladner et al. .............. | 435/69.7 |
| 5,243,041 A | 9/1993 | Fernandez-Pol ............ | 536/23.5 |
| 5,302,519 A | 4/1994 | Blackwood et al. ........ | 435/69.1 |
| 5,324,638 A | 6/1994 | Tao et al. .................... | 435/69.1 |
| 5,324,818 A | 6/1994 | Nabel et al. ................. | 530/350 |
| 5,324,819 A | 6/1994 | Oppermann et al. ........ | 530/350 |
| 5,340,739 A | 8/1994 | Stevens et al. ........... | 435/240.1 |
| 5,348,864 A | 9/1994 | Barbacid ..................... | 435/69.1 |
| 5,350,840 A | 9/1994 | Call et al. .................... | 536/23.1 |
| 5,356,802 A | 10/1994 | Chandrasegaran .......... | 435/199 |
| 5,376,530 A | 12/1994 | De The et al. ................... | 435/6 |
| 5,403,484 A | 4/1995 | Ladner et al. ........... | 435/235.1 |
| 5,436,150 A | 7/1995 | Chandrasegaran .......... | 435/199 |
| 5,487,994 A | 1/1996 | Chandrasegaran .......... | 435/199 |
| 5,498,530 A | 3/1996 | Schatz et al. .............. | 435/69.1 |
| 5,578,483 A | 11/1996 | Evans et al. .............. | 435/240.2 |
| 5,597,693 A | 1/1997 | Evans et al. ................... | 435/6 |
| 5,639,592 A | 6/1997 | Evans et al. .................... | 435/4 |
| 5,674,738 A | 10/1997 | Abramson et al. ........ | 435/252.3 |
| 5,702,914 A | 12/1997 | Evans et al. .................. | 435/29 |
| 5,789,538 A | 8/1998 | Rebar et al. ................. | 530/324 |
| 5,792,640 A | 8/1998 | Chandrasegaran .......... | 435/199 |
| 5,869,618 A | 2/1999 | Lippman et al. .......... | 530/387.1 |
| 5,871,902 A | 2/1999 | Weininger et al. ............. | 435/5 |
| 5,871,907 A | 2/1999 | Winter et al. .................... | 435/6 |
| 5,916,794 A | 6/1999 | Chandrasegaran .......... | 435/199 |
| 5,939,538 A | 8/1999 | Leavitt et al. .............. | 536/23.1 |
| 5,972,615 A | 10/1999 | An et al. ...................... | 435/6 |
| 6,001,885 A | 12/1999 | Vega et al. ................. | 514/725 |
| 6,007,988 A | 12/1999 | Choo et al. ................... | 435/6 |
| 6,013,453 A | 1/2000 | Choo et al. ................... | 435/6 |

FOREIGN PATENT DOCUMENTS

| | | |
|---|---|---|
| EP | 875 567 A2 | 11/1998 |
| GB | WO 06166 * | 2/1996 |
| WO | WO 95/19431 A1 | 7/1995 |
| WO | WO 96/06110 A1 | 2/1996 |
| WO | WO 96/06166 * | 2/1996 |
| WO | WO 96/11267 A1 | 4/1996 |
| WO | WO 96/20951 A1 | 7/1996 |
| WO | WO 96/32475 A2 | 10/1996 |
| WO | WO 97/27212 A1 | 7/1997 |
| WO | WO 97/27213 A1 | 7/1997 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 99/36553 A2 | 7/1999 |
| WO | WO 99/41371 A1 | 8/1999 |
| WO | WO 99/42474 A2 | 8/1999 |
| WO | WO 99/45132 A1 | 9/1999 |
| WO | WO 99/47656 A2 | 9/1999 |
| WO | WO 99/48909 A2 | 9/1999 |

OTHER PUBLICATIONS

Krizek Beth Allyn et al. A consensus zinc finger peptide: design, high–affinity metal binding, a pH–dependent structure, and a His to Cys sequence variant. J. Am. Chem. Soc. 1991, 113, 4518–4523.*

Bonde et al., "Ontogeny of the v–erb A Oncoprotein from the Thyroid Hormone Receptor: an Alteration in the DNA Binding Domain Plays a Role Crucial for v–erb A Function," *J. Virology*, 65(4):2037–2046 (1991).

Desjardins et al., "Repeated CT Elements Bound by Zinc Finger Proteins Control the Absolute and Relative Activities of the Two Principal Human c–myc Promoters," *Mol. and Cellular Biol.*, 13(9):5710–5724 (1993).

Hall et al., "Functional Interaction between the Two Zinc finger Domains of the v–erb A Oncoprotein," *Clee Growth & Differentiation*, 3:207–216 (1992).

Isalan et al: "Synergy between adjacent zinc fingers in sequence–specific DNA recognition" Proceedings of the National Academy of Sciences of USA, vol. 94, May 27, 1997 pp. 5617–5621, XP002075337.

(List continued on next page.)

*Primary Examiner*—Christopher S. F. Low
*Assistant Examiner*—Hope A. Robinson
(74) *Attorney, Agent, or Firm*—Townsend and Townsend and Crew LLP

(57) ABSTRACT

The invention provides a method for preparing a nucleic acid binding protein of the Cys2-His2 zinc finger class capable of binding to a nucleic acid quadruplet in a target nucleic acid sequence, wherein binding to base 4 of the quadruplet by an alpha-helical zinc finger nucleic acid binding motif in the protein is determined as follows: if base 4 in the quadruplet is A, then position +6 in the alpha-helix is Glu, Asn or Val; if base 4 in the quadruplet is C, then position +6 in the alpha-helix is Ser, Thr, Val, Ala, Glu or Asn.

25 Claims, 8 Drawing Sheets

OTHER PUBLICATIONS

Agarwal et al., "Stimulation of Transcript Elongation Requires Both the Zinc Finger and RNA Polymerase II Binding Domains of Human TFIIS," *Biochemistry*, 30(31):7842–7851 (1991).

Anato et al., "A thermodynamic study of unusually stable RNA and DNA hairpins," *Nuc. Acids. Res.*, 19(21):5901–5905 (1991).

Barbas, C. F., "Recent advances in phage display," *Curr. Opin. Biotech.*, 4:526–530 (1993).

Barbas et al., "Assembly of combinatorial antibody libraries on phage surfaces: The gene III site," *PNAS*, 88:7978–7982 (1991).

Barbas et al., "Semisynthetic combinatorial antibody libraries: A chemical solution to the diversity problem," *PNAS*, 89:4457–4461 (1992).

Bellefroid et al., "Clustered organization of homologous KRAB zinc–finger genes with enhanced expression in human T lymphod cells," *EMBO J.*, 12(4):1363–1374 (1993).

Berg, J.M., "DNA Binding Specificity of Steroid Receptors," *Cell*, 57:1065–1068 (1989).

Berg, J.M., "Sp1 and the subfamily of zinc–finger proteins with guanine–rich binding sites," *PNAS*, 89:11109–11110 (1992).

Berg et al., "The Galvanization of Biology: A Growing Appreciation for the Roles of Zinc," *Science*, 271:1081–1085 (1996).

Berg, J.M., "Letting your fingers do the walking," *Nature Biotechnology*, 15:323 (1997).

Bergqvist et al., "Loss of DNA–binding and new transcriptional trans–activation function in polyomavirus large T–angtigen with mutation of zinc finger motif," *Nuc. Acids Res.*, 18(9):2715–2720 (1990).

Blaese et al., "Vectors in cancer therapy: how will they deliver?," *Cancer Gene Therapy*, 2(4):291–297 (1995).

Caponigro et al., "Transdominant genetice analysis of a growth control pathway," *PNAS*, 95:7508–7513 (1998).

Celenza et al., "A Yeast Gene That Is Essential for Release from Glucose Repression Encodes a Protein Kinase," *Science*, 233:1175–1180 (1986).

Cheng et al., "Identification of Potential Target Genes for Adr1p through Characterization of Essential Nucleotides in UAS1," *J. Mol. Cellular Biol.*, 14(6):3842–3852 (1994).

Cheng et al., "A Single Amino Acid Substitution in Zinc Finger 2 of Adr1p Changes its Binding Specificity at two Positions in UAS1,"*J. Mol. Biol.*, 251:1–8 (1995).

Choo et al., A role in DNA Binding for the linker sequences of the first three zinc fingers of TFIIIA *Nuc. Acids Res.*, 21(15):3341–3346 (1993).

Choo et al., "Designing DNA–binding proteins on the surface of filamentous phage," *Curr. Opin. Biotech*, 6:431–436 (1995).

Choo et al., "Promoter–specific Activation of Gene Expression Directed by Bacteriophage–selected Zinc Fingers," *J. Mol. Biol.*, 273:525–532 (1997).

Choo, Y., "Recognition of DNA methylation by zinc fingers," *Nature Struct Biol.*, 5(4):264–265 (1998).

Choo et al., "All wrapped up," *Nature Structural Biology*, 5(4):253–255 (1998).

Choo, Y., "End effects in DNA recognition by zinc finger arrays," *Nuc. Acids. Res.*, 26(2):554–557 (1998).

Choo et al., "In vivo repression by a site–specific DNA–binding protein designed against an oncogenic sequence," *Nature*, 372:642–645 (1994).

Corbi et al., "Synthesis of a New Zinc Finger Peptide: Comparison of Its 'Code' Deduced and 'CASTing' Derived Binding Sites," *FEBS Letters*, 417:71–74 (1997).

Crozatier et al., "Single Amino Acid Exchanges in Separate Domains of the Drosophila serendipity δ Zinc Finger Protein Cause Embroyonic and Sex Biased Lethality," *Genetics*, 131:905–916 (1992).

Debs et al., Regulation of Gene Expression in Vivo by Liposome–Mediated Delivery of a Purified Transcription Factor, *J. Biological Chemistry*, 265(18):10189–10192 (1990).

Desjarlais, et al., "Length–Encoded multiplex binding site determination: Application to zinc finger proteins," *PNAS*, 91:11099–11103 (1994).

Desjarlais, et al., "Use of a zinc–finger consensus sequence framework and specificity rules to design specific DNA Binding Proteins," *PNAS*, 90:2256–2260 (1993).

Desjarlais, et al., "Toward rules relating zinc finger protein sequences and DNA binding preferences," *PNAS*, 89(16):7345–7349 (1992).

Desjarlais et al., "Redesigning the DNA–Binding Specificity of a Zinc Finger Protein: A Data Base–Guided Approach," *Proteins: Structure, Function, and Genetics*, 12(2):101–104 (1992).

Desjarlais et al., "Redesigning the DNA–Binding Specificity of a Zinc Finger Protein: A Data Base–Guided Approach," *Proteins: Structure, Function, and Genetics*, 13:272 (1992).

Dibello et al., "The Drosophila Broad–Complex Encodes a Family of Related Proteins Containing Zinc Fingers," *Genetics*, 129:385–397 (1991).

Elrod–Erickson et al., "High–resolution structures of variant Zif268–DNA complexes: implications for understanding zinc finger–DNA recognition," *Structure*, 6(4):451–464 (1998).

Fairall et al., "The crystal structure of a two zinc–finger peptide reveals an extension to the rules for zinc–finger/DNA recognition," *Nature*, 366:483–487 (1993).

Frankel et al., "Fingering Too Many Proteins," *Cell*, 53:675 (1988).

Friesen et al., "Phage Display of RNA Binding Zinc Fingers from Transcription Factor IIA*," *J. Biological Chem.*, 272(17):10994–10997 (1997).

Ghosh, D., "A relational database of transcription factors," *Nuc. Acids Res.*, 18(7):1749–1756 (1990).

Gogos et al., "Recognition of diverse sequences by class I zinc fingers: Asymmetries and indirect effects on specificity in the interaction between CF211 and A+T–rich sequences elements," *PNAS*, 93(5):2159–2164 (1996).

Gossen et al., "Tight control of gene expression in mammalian cells by tetracycline–responsive promoter," *PNAS*, 89:5547–5551 (1992).

Greisman & Pabo, "A General Strategy for Selecting High–Affinity Zinc Finger Proteins for Diverse DNA Target Sites," *Science*, 275:657–561 (1997).

Hamilton et al., "High affinity binding sites for the Wilms' tumor suppressor protein WTI," *Nuc. Acids. Res.*, 23(2):277–284 (1995).

Hamilton et al., "Comparison of the DNA Binding Characteristics of the Related Zinc Finger Proteins WT1 and EGR1," *Biochemistry*, 37:2051–2058 (1998).

Hanas et al., "Internal deletion mutants of Xenopus transcription factor IIIA," *Nuc. Acids. Res.*, 17(23):9861–9870 (1989).

Hayes et al., "Locations of Contacts Between Individual Zinc Fingers *Xenopus laevis*, Transcription Factor IIIA and the Internal Control Region of a 5S RNA Gene," *Biochemistry*, 31:11600–11605 (1992).

Heinzel et al., "A complex containing N–CoR, MSin3 and histone deacetylase medates transcriptional repression," *Nature*, 387:43–48 (1997).

Hirst et al., "Discrimination of DNA response elements for thyroid hormone and estrogen is dependent of dimmerization of receptor DNA binding domains," *PNAS*, 89:5527–5531 (1992).

Hoffman et al., "Structures of DNA–binding mutant zinc finger domains: implications for DNA binding," *Protein Science*, 2:951–965 (1993).

Isalan et al., "Comprehensive DNA Recognition Through Concerted Interactions from Adjacent Zinc Fingers," *Biochemistry*, 37:12026–12033 (1998).

Jacobs, G.H., "Determination of the base recognition positions of zinc fingers from sequence analysis," *EMBO J.*, 11(12):4507–4517 (1992).

Jamieson et al. "A zinc finger directory for high–affinity DNA recognition," *PNAS*, 93:12834–12839 (1996).

Jamieson et al., "In Vitro Selection of Zinc Fingers with Altered DNA–Binding Specificity," *Biochemistry*, 33(19):5689–5695 (1994).

Julian et al., "Replacement of His23 by Cys in a zinc finger of HIV–1 NCp7 led to a change in 1H NMR–derived 3D structure and to a loss of biological activity," *FEBS Letters*, 331(1,2):43–48 (1993).

Kamiuchi et al., "New multi zinc finger protein: biosynthetic design and characteristics of DNA recognition," *Nucleic Acids Symposium Series*, 37:153–154 (1997).

Kim et al., "Serine at Position 2 in the DNA Recognition helix of a Cys2–His2 Zinc finger Peptide is Not, in General, Responsible for Base Recognition," *J. Mol. Biol.*, 252:1–5 (1995).

Kim et al., "Site–Specific cleavage of DNA–RNA hybrids by zinc finger/FokI cleavage domain fusions," *Gene*, 203:43–49 (1997).

Kim et al., "A 2.2 A° resolution crystal structure of a designed zinc finger protein bound to DNA," *Nat. Struct. Biol.*, 3(11):940–945 (1996).

Kim et al., "Getting a handhold on DNA: Design of poly–zinc finger proteins with femtomolar dissociation constants," *PNAS*, 95:2812–2817 (1998).

Kim et al., "Design of TATA box–binding protein/zinc finger fusions for targeted regulation of gene expression," *PNAS*, 94:3616–3620 (1997).

Kim et al., "Hybrid restriction enzymes: Zinc finger fusions Fok I cleavage domain," *PNAS*, 93:1156–1160 (1996).

Kim, J.S. and Pabo, C.O., "Transcriptional repression by zinc finger peptides," *J. Biol. Chem.*, 272(47):29795–28000 (1997).

Kinzler et al., "The GLI gene is member of the Kruppel family of zinc finger proteins," *Nature*, 332:371–4 (1988).

Klug, A., "Gene Regulatory Proteins and Their Interaction with DNA," *Ann. NY Acad. Sci.*, 758:143–160 (1995).

Klug et al., "Protein Motifs 5: Zinc Fingers," *FASEB J.*, 9:597–604 (1995).

Kothekar, "Computer simulation of zinc finger motifs from cellular nucleic acid binding proteins and their interaction with consensus DNA sequences," *FEBS Letters*, 274(1–2):217–222 (1990).

Kriwacki et al., "Sequence–specific recognition of DNA by zinc–finger peptides derived from the transcription factor Sp1," *PNAS*, 89:9759–9763 (1992).

Kulda et al., "The regulatory gene areA mediating nitrogen metabolite repression in *Aspergillus nidulans*, Mutations affecting specificity of gene activation alter a loop residue of putative zinc finger," *EMBO J.*, 9(5):1355–1364 (1990).

Liu et al., "Design of polydactyl zinc–finger proteins for unique addressing within complex genomes," *PNAS*, 94(11):5525–5530 (1997).

Mandel–Gutfreund et al., "Quantitative parameters for amino acid–base interaction: Implication for predication of protein–DNA binding sites," *Nuc. Acids Res.*, 26(10):2306–2313 (1998).

Margolin et al., "Kruppel–associated boxes are potent transcriptional repression domains," *PNAS*, 91:4509–4513 (1994).

Mizushima et al., "pEF–BOS, a powerful mammilian expression vector," *Nuc. Acids. Res.*, 18(17):5322 (1990).

Nakagama et al., "Sequence and structural requirements for High–Affinity DNA Binding by the WT1 Gene Product," *Molecular and Cellular Biology*, 15(3):1489–1498 (1995).

Nardelli et al., "Zinc finger–DNA recognition: analysis of base specificity by site–directed mutagenesis," *Nuc Acids Res.*, 20(16):4137–4144 (1992).

Nardelli et al., "Base sequence discrimination by zinc–finger DNA–binding domains," *Nature*, 349:175–178 (1991).

Nekludova et al., "Distinctive DNA conformation with enlarged major groove is found in Zn–finger–DNA and other protein–DNA complexes," *PNAS*, 91:6948–6952 (1994).

Orkin et al., "Report and Recommendations of the Panel to Assess the NIH Investment in Research on Gene Therapy," Dec. 7. 1995.

Pabo et al., "Systematic Analysis of Possible Hydrogen Bonds between Amino Acid Side Chains and B–form DNA," *J. Biomolecular Struct. Dynamics*, 1:1039–1049 (1983).

Pabo et al., "Protein–DNA Recognition," *Ann. Rev. Biochem.*, 53:293–321 (1984).

Pabo, C. O., "Transcription Factors: Structural Families and Principals of DNA Recognition," *Ann. Rev. Biochem.*, 61:1053–1095 (1992).

Pavletich et al., "Crystal Structure of a Five–Finger GLI–DNA Complex: New Perspectives on Zinc Fingers," *Science*, 261:1701–1707 (1993).

Pavletich et al., "Zinc Finger–DNA Recognition: Crystal Structure of a Zif268–DNA Complex at 2.1 A," *Science*, 252:809–817 (1991).

Pengue et al., "Repression of transcriptional activity at a distance by the evolutionarily conserved KRAB domain present in a subfamily of zinc finger proteins," *Nuc. Acids Res.*, 22(15):2908–2914 (1994).

Pengue et al., "Transcriptional Silencing of Human Immunodeficiency Virus Type I Long Terminal Repeat–Driven Gene Expression by the Kruppel–Associated Box Repressor Domain Targeted to the Transactivating Response Element," *J. Virology*, 69(10):6577–6580 (1995).

Pengue et al., "Kruppel–associated box–mediated repression of RNA polymerase II promoters is influenced by the arrangement of basal promoter elements," PNAS, 93:1015–1020 (1996).

Pommerantz et al., "Structure–Based Design of a Dimeric Zinc Finger Protein," Biochemistry, 37(4):965–970 (1998).

Pommerantz et al., "Structure–Based Design of Transcription Factors," Science, 267:93–96 (1995).

Pommerantz et al., "Analysis of homeodomain function by structure–based design of a transciption factor," PNAS, 92:9752–9756 (1995).

Qian et al., "Two–Dimensional NMR Studies of the Zinc Finger Mofit: Solution Structures and Dynamics of Mutant ZFY Domains Containing Aromatic Substitutions in the Hydrophobic Core," Biochemistry, 31:7463–7476 (1992).

Quigley et al., "Complete Androgen Insensitivity Due to Deletion of Exon C of the Androgen Receptor Gene Highlights the Functional Importance of the Second Zinc Finger of the Androgen Receptor In Vivo," Molecular Endocrinology, 6(7):1103–1112 (1992).

Rauscher et al., "Binding of the Wilms' Tumor Locus Zinc Finger Protein to the EGR–1 Consensus Sequence," Science, 250:1259–1262 (1990).

Ray et al., "Repressor to activator switch by mutations in the first Zn finger of the glucocorticoid receptor: Is direct DNA binding necessary?," PNAS, 88:7086–7090 (1991).

Rebar et al., "Phage Display Methods for Selecting Zinc Finger Proteins with Novel DNA–Binding Specificities," Methods in Enzymology, 267:129–149 (1996).

Rebar et al., "Zinc Finger Phage: Affinity Selection of Fingers With New DNA–Binding Specifities," Science, 263:671–673 (1994).

Reith et al., "Cloning of the major histocompatibility complex class II promoter binding protein affected in a hereditary defect in class II gene regulation," PNAS, 86:4200–4204 (1989).

Rhodes et al., "Zinc Fingers: They play a key part in regulating the activity of genes in many species, from yeast to humans. Fewer than 10 years ago no one knew they existed," Scientific American, 268:56–65 (1993).

Rice et al., "Inhibitors of HIV Nucleocapsid Protein Zinc Fingers as Candidates for the Treatment of AIDS," Science, 270:1194–1197 (1995).

Rivera et al., "A humanized system for pharmacologic control of gene expression," Nature Medicine, 2(9):1028–1032 (1996).

Rollins et al., "Role of TFIIIA Zinc Fingers In vivo: Analysis of Single–Finger Function in Developing Xenopus Embyros," Molecular Cellular Biology, 13(8):4776–4783 (1993).

Saleh et al., "A Novel Zinc Finger Gene on Human Chromosome 1 qter That is Alternatively Spliced in Human Tissues and Cell Lines," Am. J. Hum. Genet., 52:192–203 (1993).

Shi et al., "Specific DNA–RNA Hybrid Binding by Zinc Finger Proteins," Science, 268:282–284 (1995).

Shi et al., "DNA Unwinding Induced by Zinc Finger Protein Binding," Biochemistry, 35:3845–3848 (1996).

Shi et al., "A direct comparison of the properties of natural and designed finger proteins," Chem., & Biol., 2(2):83–89 (1995).

Singh et al., "Molecular Cloning of an Enhancer Binding Protein: Isolation by Screening of an Expression Library with a Recognition Site DNA," Cell, 52:415–423 (1988).

Skerka et al., "Coordinate Expression and Distinct DNA–Binding Characteristics of the Four EGR–Zinc Finger Proteins in Jurkat T Lymphocytes," Immunobiology, 198:179–191 (1997).

South et al., "The Nucleocapsid Protein Isolated from HIV–1 Particles Binds Zinc and Forms Retroviral–Type Zinc Fingers," Biochemistry, 29:7786–7789 (1990).

Suzuki et al., "Stereochemical basis of DNA recognition by Zn fingers," Nuc. Acids Res., 22(16):3397–3405 (1994).

Suzuki et al. "DNA recognition code of transcription factors in the helix–turn–helix, probe helix, hormone receptor, and zinc finger families," PNAS, 91:12357–12361 (1994).

Swirnoff et al., "DNA–Binding Specificity of NGFI–A and Related Zinc Finger Transcription Factors," Mol. Cell. Biol., 15(4):2275–2287 (1995).

Taylor et al., "Designing Zinc–Finger ADRI Mutants with Altered Specificity of DNA Binding to T in UASI Sequences," Biochemistry, 34:3222–3230 (1995).

Thiesen et al., "Determination of DNA binding specificities of mutated zinc finger domains," FEBS Letters, 283(1):23–26 (1991).

Thiesen et al., "Amino Acid Substitutions in the SP1 Zinc Finger Domain Alter the DNA Binding Affinity to Cognate SP1 Target Site," Biochem. Biophys. Res. Communications, 175(1):333–338 (1991).

Thukral et al., "Localization of a Minimal Binding Domain and Activation Regions in Yeast Regulaory Protein ADRI1," Molecular Cellular Biology, 9(6):2360–2369 (1989).

Thukral et al., "Two Monomers of Yeast Transcription Factor ADR1 Bind a Palindromic Sequence Symmetrically to Activate ADH2 Expression," Molecular Cellular Biol., 11(3):1566–1577 (1991).

Thukral et al., "Alanine scanning site–directed mutagenesis of the zinc fingers of transcription factor ADR1: Residues that contact DNA and that transactivate," PNAS, 88:9188–9192 (1991) + correction page.

Thukral et al., "Mutations in the Zinc Fingers of ADR1 That Change the Specificity of DNA Binding and Transactivation," Mol. Cell Biol., 12(6):2794–2792 (1992).

Vortkamp et al., "Identification of Optimized Target Sequences for the GL13 Zinc Finger Protein," DNA Cell Biol., 14(7):629–634 (1995).

Webster et al., "Conversion of the E1A Cys4 zinc finger to a nonfunctional His2, Cys2 zinc finger by a single point mutation," PNAS, 88:9989–9993 (1991).

Whyatt et al., "The two zinc finger–like domains of GATA–1 have different DNA binding specificities," EMBO J., 12(13):4993–5005 (1993).

Wilson et al., "In Vivo Mutational analysis of the NGFI–A Zinc Fingers," J. Biol. Chem., 267(6):3718–3724 (92).

Witzgall et al., "The Kruppel–associated box–A (KRAB–A) domain of zinc finger proteins mediates transcriptional repression," PNAS, 91:4514–4518 (1994).

Wright et al., "Expression of Zinc Finger Gene in HTLV–1 and HTLV–II–transformed Cells," Science, 248:588–591 (1990).

Wu et al., "Building zinc fingers by selection: Toward a therapeutic application," PNAS, 92:344–348 (1995).

Yang et al., "Surface plasmon resonance based kinetic studies of zinc finger–DNA interactions," J. Immunol. Methods, 183:715–182 (1995).

Yu et al., "A hairpin ribozyme inhibits expression of diverse strains of human immunodeficiency virus type 1," PNAS, 90:6340–6344 (1993).

* cited by examiner

```
                        -1 1 2 3 4 5 6 7 8 9
F1  M A E E R P Y A G P V E S C D R R F S C D R R F S R S D E L T R H I R I H  T G Q K P
F2              F Q C R I - - C M R N F S R S D D L T H I R T H  T G E K P
F3              F A C D I - - C G R K F A S D R K R H T K I H  L R Q K D
                        β           β              α - helix
```

```
         8    9   10   11   12   13   14   15   16
Wild-type 5' GTG GTG GGC GCC GGC GGT GTG GGC AAG 3'
          3' CAC CAC CCG CGG CCG CCA CAC CCG TTC 5'
                              ↓
EJ mutant 5' GTG GTG GGC GCC GGC GGT GTG GGC AAG 3'
          3' CAC CAC CCG CGG CAG CCA CAC CCG TTC 5'
```

FIG. 6C

```
              -1  1  2  3  4  5  6  7  8  9
F1  M A E E K P F Q C R I C M R N F S D R S S L T R H T G E K P
F2          F Q C R I C M R N F S D R S S L T R H T G E K P
F3          F Q C R I C M R N F S D R S S L T R H T G E K P
              β        β                α - helix
```

NUCLEIC ACID BINDING PROTEINS

This application is the national phase of international application PCT/GB98/01512 filed May 26, 1998 which designated the U.S.

The present invention relates to nucleic acid binding proteins. In particular, the invention relates to a method for designing a protein which is capable of binding to any predefined nucleic acid sequence.

Protein-nucleic acid recognition is a commonplace phenomenon which is central to a large number of biomolecular control mechanisms which regulate the functioning of eukaryotic and prokaryotic cells. For instance, protein-DNA interactions form the basis of the regulation of gene expression and are thus one of the subjects most widely studied by molecular biologists.

A wealth of biochemical and structural information explains the details of protein-DNA recognition in numerous instances, to the extent that general principles of recognition have emerged. Many DNA-binding proteins contain independently folded domains for the recognition of DNA, and these domains in turn belong to a large number of structural families. such as the leucine zipper, the "helix-turn-helix" and zinc finger families.

Despite the great variety of structural domains, the specificity of the interactions observed to date between protein and DNA most often derives from the complementarity of the surfaces of a protein α-helix and the major groove of DNA [Klug, (1993) Gene 135:83–92]. In light of the recurring physical interaction of α-helix and major groove, the tantalising possibility arises that the contacts between particular amino acids and DNA bases could be described by a simple set of rules; in effect a stereochemical recognition code which relates protein primary structure to binding-site sequence preference.

It is clear, however, that no code will be found which can describe DNA recognition by all DNA-binding proteins. The structures of numerous complexes show significant differences in the way that the recognition α-helices of DNA-binding proteins from different structural families interact with the major groove of DNA, thus precluding similarities in patterns of recognition. The majority of known DNA-binding motifs are not particularly versatile. and any codes which might emerge would likely describe binding to a very few related DNA sequences.

Even within each family of DNA-binding proteins. moreover, it has hitherto appeared that the deciphering of a code would be elusive. Due to the complexity of the protein-DNA interaction. there does not appear to be a simple "alphabetic" equivalence between the primary structures of protein and nucleic acid which specifies a direct amino acid to base relationship.

International patent application WO 96/06166 addresses this issue and provides a "syllabic" code which explains protein-DNA interactions for zinc finger nucleic acid binding proteins. A syllabic code is a code which relies on more than one feature of the binding protein to specify binding to a particular base, the features being combinable in the forms of "syllables", or complex instructions, to define each specific contact.

However, this code is incomplete, providing no specific instructions permitting the specific selection of nucleotides other than G in the 5' position of each triplet. The method relies on randomisation and subsequent selection in order to generate nucleic acid binding proteins for other specificities. Even with the aid of partial randomisation and selection, however, neither the method reported in WO 96/06166 nor any other methods of the prior art have succeeded in isolating a zinc finger polypeptide based on the first finger of Zif268 capable of binding triplets wherein the 5' base is other than G or T. This is a serious shortfall in any ability to design zinc finger proteins.

Moreover, this document relies upon the notion that zinc fingers bind to a nucleic acid triplet or multiples thereof, as does all of the prior art. We have now determined that zinc finger binding sites are determined by overlapping 4 bp subsites, and that sequence-specificity at the boundary between subsites arises from synergy between adjacent fingers. This has important implications for the design and selection of zinc fingers with novel DNA binding specificities.

SUMMARY OF THE INVENTION

The present invention provides a more complete code which permits the selection of any nucleic acid sequence as the target sequence. and the design of a specific nucleic acid-binding protein which will bind thereto. Moreover, the invention provides a method by which a zinc finger protein specific for any given nucleic acid sequence may be designed and optimised. The present invention therefore concerns a recognition code which has been elucidated for the interactions of classical zinc fingers with nucleic acid. in this case a pattern of rules is provided which covers binding to all nucleic acid sequences.

The code set forth in the present invention takes account of synergistic interactions between adjacent zinc fingers. thereby allowing the selection of any desired binding site.

According to a first aspect of the present invention. therefore, we provide a method for preparing a nucleic acid binding protein of the Cys2-His2 zinc finger class capable of binding to a nucleic acid quadruplet in a target nucleic acid sequence, wherein binding to base 4 of the quadruplet by an α-helical zinc finger nucleic acid binding motif in the protein is determined as follows:

a) if base 4 in the quadruplet is A. then position +6 in the α-helix is Glu. Asn or Val;

b) if base 4 in the quadruplet is C, then position +6 in the α-helix is Ser, Thr, Val, Ala, Glu or Asn.

Preferably, binding to base 4 of the quadruplet by an α-helical zinc finger nucleic acid binding motif in the protein is additionally determined as follows:

c) if base 4 in the quadruplet is G, then position +6 in the α-helix is Arg or Lys;

d) if base 4 in the quadruplet is T. then position +6 in the α-helix is Set, Thr, Val or Lys.

The quadruplets specified in the present invention are overlapping, such that, when read 3' to 5' on the -strand of the nucleic acid, base 4 of the first quadruplet is base 1 of the second, and so on. Accordingly, in the present application, the bases of each quadruplet are referred by number, from 1 to 4, 1 being the 3' base and 4 being the 5' base. Base 4 is equivalent to the 5' base of a classical zinc finger binding triplet.

All of the nucleic acid-binding residue positions of zinc fingers, as referred to herein, are numbered from the first residue in the α-helix of the finger, ranging from +1 to +9. "−1" refers to the residue in the framework structure immediately preceding the α-helix in a Cys2-His2 zinc finger polypeptide.

Residues referred to as "++2" are residues present in an adjacent (C-terminal) finger. They reflect the synergistic cooperation between position +2 on base 1 (on the + strand) and position +6 of the preceding (N-terminal) finger on base 4 of the preceding (3') quadruplet, which is the same base due to the overlap. Where there is no C-terminal adjacent finger, "++" interactions do not operate.

Cys2-His2 zinc finger binding proteins, as is well known in the art, bind to target nucleic acid sequences via α-helical zinc metal atom coordinated binding motifs known as zinc fingers. Each zinc finger in a zinc finger nucleic acid binding protein is responsible for determining binding to a nucleic acid quadruplet in a nucleic acid binding sequence. Preferably, there are 2 or more zinc fingers, for example 2, 3, 4, 5 or 6 zinc fingers, in each binding protein. Advantageously, there are 3 zinc fingers in each zinc finger binding protein.

The method of the present invention allows the production of what are essentially artificial nucleic acid binding proteins. In these proteins, artificial analogues of amino acids may be used, to impart the proteins with desired properties or for other reasons. Thus, the term "amino acid", particularly in the context where "any amino acid" is referred to, means any sort of natural or artificial amino acid or amino acid analogue that may be employed in protein construction according to methods known in the an. Moreover, any specific amino acid referred to herein may be replaced by a functional analogue thereof, particularly an artificial functional analogue. The nomenclature used herein therefore specifically comprises within its scope functional analogues of the defined amino acids.

The α-helix of a zinc finger binding protein aligns antiparallel to the nucleic acid strand, such that the primary nucleic acid sequence is arranged 3' to 5' in order to correspond with the N terminal to C-terminal sequence of the zinc finger. Since nucleic acid sequences are conventionally written 5' to 3', and amino acid sequences N-terminus to C-terminus, the result is that when a nucleic acid sequence and a zinc finger protein are aligned according to convention, the primary interaction of the zinc finger is with the—strand of the nucleic acid. since it is this strand which is aligned 3' to 5'. These conventions are followed in the nomenclature used herein. It should be noted, however, that in nature certain fingers, such as finger 4 of the protein GLI, bind to the + strand of nucleic acid: see Suzuki et al., (1994) NAR 22:3397–3405 and Pavletich and Pabo, (1993) Science 261:1701–1707. The incorporation of such fingers into nucleic acid binding molecules according to the invention is envisaged.

The invention provides a solution to a problem hitherto unaddressed in the art, by permitting the rational design of polypeptides which will bind nucleic acid quadruplets whose 5' residue is other than G. In particular, the invention provides for the first time a solution for the design of polypeptides for binding quadruplets containing 5' A or C.

BRIEF DESCRIPTION OF THE DRAWINGS

FIG. 2 shows the amino acid sequence of three fingers (SEQ ID NOS: 12–14, respectively in order of appearance) used for phage display selection in the determination of recognition code.

FIG. 3 lists the sequence-specific zinc finger clones (SEQ ID NOS: 15–109, respectively in order of appearance) obtained from phage selections, and their binding site signatures.

DETAILED DESCRIPTION OF THE INVENTION

Figure 1:
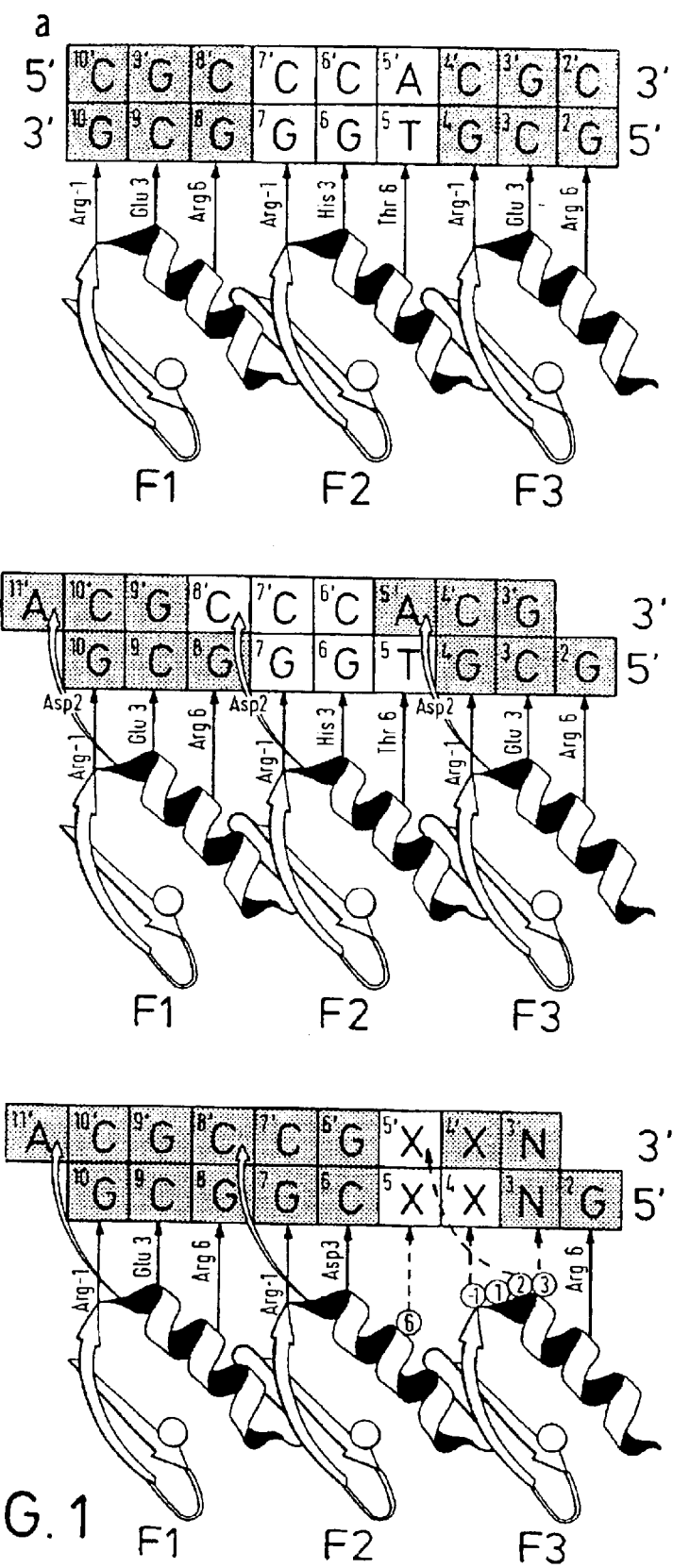
FIG. 1 illustrates zinc finger-DNA interactions. A: model of classical triplet interactions with DNA base triplets in Zif268; B: similar model showing quadruplet interactions; C: model of library design for recognition code determination.

Position +6 in the α-helix is generally responsible for the interaction with the base 4 of a given quadruplet in the target. According to the present invention, an A at base 4 interacts with Gln, Asn or Val at position +6, while a C at base 4 will interact with Ser, Thr, Val, Ala, Glu or Asn.

The present invention concerns a method for preparing nucleic acid binding proteins which are capable of binding nucleic acid. Thus, whilst the solutions provided by the invention will result in a functional nucleic acid binding molecule, it is possible that naturally-occurring zinc finger nucleic acid binding molecules may not follow some or all of the rules provided herein. This does not matter, because the aim of the invention is to permit the design of the nucleic acid binding molecules on the basis of nucleic acid sequence, and not the converse. This is why the rules, in certain instances, provide for a number of possibilities for any given residue. In other instances, alternative residues to those given may be possible. The present invention, thus, does not seek to provide every solution for the design of a binding protein for a given target nucleic acid. It does, however, provide for the first time a complete solution allowing a functional nucleic acid binding protein to be constructed for any given nucleic acid quadruplet.

In a preferred aspect, therefore, the invention provides a method for preparing a nucleic acid binding protein of the Cys2-His2 zinc finger class capable of binding to a nucleic acid quadruplet in a target nucleic acid sequence, wherein binding to each base of the quadruplet by an α-helical zinc finger nucleic acid binding motif in the protein is determined as follows:

a) if base 4 in the quadruplet is G, then position +6 in the α-helix is Arg or Lys;

b) if base 4 in the quadruplet is A, then position +6 in the α-helix is Glu, Asn or Val;

c) if base 4 in the quadruplet is T, then position +6 in the α-helix is Ser, Thr, Val or Lys;

d) if base 4 in the quadruplet is C, then position +6 in the α-helix is Ser, Thr, Val, Ala, Glu or Asn;

e) if base 3 in the quadruplet is G, then position +3 in the α-helix is His;

f) if base 3 in the quadruplet is A, then position +3 in the α-helix is Asn;

g) if base 3 in the quadruplet is T, then position +3 in the α-helix is Ala, Ser or Val; provided that if it is Ala, then one of the residues at −1 or +6 is a small residue;

h) if base 3 in the quadruplet is C, then position +3 in the α-helix is Ser, Asp, Glu, Leu, Thr or Val;

i) if base 2 in the quadruplet is G, then position −1 in the α-helix is Arg;

j) if base 2 in the quadruplet is A, then position −1 in the α-helix is Gln;

k) if base 2 in the quadruplet is T, then position −1 in the α-helix is His or Thr;

l) if base 2 in the quadruplet is C, then position −1 in the α-helix is Asp or His;

m) if base 1 in the quadruplet is G, then position +2 is Glu;

n) if base 1 in the quadruplet is A, then position +2 is Arg or Gln;

o) if base 1 in the quadruplet is C, then position +2 is Asn, Gln, Arg, His or Lys;

p) if base 1 in the quadruplet is T, then position +2 is Ser or Thr.

The foregoing represents a set of rules which permits the design of a zinc finger binding protein specific for an), given nucleic acid sequence. A novel finding related thereto is that position +2 in the helix is responsible for determining the binding to base 1 of the quadruplet. In doing so, it cooperates synergistically with position +6. which determines binding at base 4 in the quadruplet, bases 1 and 4 being overlapping in adjacent quadruplets.

Although zinc finger polypeptides are considered to bind to overlapping quadruplet sequences, the method of the present invention allows polypeptides to be designed to bind to target sequences which are not multiples of overlapping quadruplets. For example, a zinc finger polypeptide may be designed to bind to a palindromic target sequence. Such sequences are commonly found as, for example, restriction enzyme target sequences.

Preferably, creation of zinc fingers which bind to fewer than three nucleotides is achieved by specifying, in the zinc finger, amino acids which are unable to support H-bonding with the nucleic acid in the relevant position.

Advantageously, this is achieved by substituting Gly at position −1 (to eliminate a contact with base 2) and/or Ala at positions +3 and/or +6 (to eliminate contacts at the 3rd or 4th base respectively).

Preferably, the contact with the final (3') base in the target sequence should be strengthened, if necessary, by substituting a residue at the relevant position which is capable of making a direct contact with the phosphate backbone of the nucleic acid.

A zinc finger binding motif is a structure well known to those in the art and defined in, for example, Miller et at., (1985) EMBO J. 4:1609–1614; Berg (1988) PNAS (USA) 85:99–102: Lee er at., (1989) Science 245:635–637; see International patent applications WO 96/06166 and WO 96132475, corresponding to U.S. Ser. No. 08/422.107, incorporated herein by reference.

As used herein, "nucleic acid" refers to both RNA and DNA, constructed from natural nucleic acid bases or synthetic bases, or mixtures thereof. Preferably, however, the binding proteins of the invention are DNA binding proteins.

In general, a preferred zinc finger framework has the structure (SEQ ID NO: 3):

$$X_{0-2} \: C \: X_{1-5} \: C \: X_{9-14} \: H \: X_{3-6} \: H/C \qquad (A)$$

where X is any amino acid, and the numbers in subscript indicate the possible numbers of residues represented by X.

In a preferred aspect of the present invention, zinc finger nucleic acid motifs may be represented as motifs having the following primary structure (SEQ ID NO: 4):

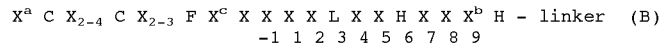

$$X^a \: C \: X_{2-4} \: C \: X_{2-3} \: F \: X^c \: X \: X \: X \: X \: L \: X \: X \: H \: X \: X \: X^b \: H - \text{linker} \qquad (B)$$
$$\phantom{X^a \: C \: X_{2-4} \: C \: X_{2-3} \: F \: X^c} -1 \: 1 \: 2 \: 3 \: 4 \: 5 \: 6 \: 7 \: 8 \: 9$$

wherein X (including $X^a$, $X^b$ and $X^c$) is any amino acid. $X_{2-4}$ and $X_{2-3}$ refer to the presence of 2 or 4, or 2 or 3, amino acids, respectively. The Cys and His residues, which together co-ordinate the zinc metal atom, are marked in bold text and are usually invariant, as is the Leu residue at position +4 in the α-helix.

Modifications to this representation may occur or be effected without necessarily abolishing zinc finger function, by insertion, mutation or deletion of amino acids. For example it is known that the second His residue may be replaced by Cys (Krizek et al., (1991) J. Am. Chem. Soc. 113:4518–4523) and that Leu at +4 can in some circumstances be replaced with Arg. The Phe residue before $X_c$ may be replaced by any aromatic other than Trp. Moreover, experiments have shown that departure from the preferred structure and residue assignments for the zinc finger are tolerated and may even prove beneficial in binding to certain nucleic acid sequences. Even taking this into account, however, the general structure involving an α-helix co-ordinated by a zinc atom which contacts four Cys or His residues, does not alter. As used herein, structures (A) and (B) above are taken as an exemplary structure representing all zinc finger structures of the Cys2-His2 type.

Preferably, $X^4$ is F/γ-X or P-F/γ-X. In this context, X is any amino acid. Preferably, in this context X is E, K, T or S. Less preferred but also envisaged are Q, V, A and P. The remaining amino acids remain possible.

Preferably. $X_{2-4}$ consists of two amino acids rather than four. The first of these amino acids may be any amino acid, but S, E, K, T, P and R are preferred. Advantageously, it is P or R. The second of these amino acids is preferably E, although any amino acid may be used.

Preferably, $X^b$ is T or I.

Preferably, $X^c$ is S or T.

Preferably, $X_{2-3}$ is G-K-A, G-K-C, G-K-S or G-K-G. However, departures from the preferred residues are possible, for example in the form of M-R-N (SEQ ID NO: 4) or (SEQ ID NO: 5) M-R.

Preferably, the linker is T-G-E-K or T-G-E-K-P.

As set out above, the major binding interactions occur with amino acids −1, +2, +3 and +6. Amino acids +4 and +7 are largely invariant. The remaining, amino acids may be essentially any amino acids. Preferably, position +9 is occupied by Arg or Lys. Advantageously, positions +1, +5 and +8 are not hydrophobic amino acids, that is to say are not Phes Trp or Tyr.

In a most preferred aspect, therefore, bringing together the above, the invention allows the definition of every residue in a zinc finger nucleic acid binding motif which will bind specifically to a given nucleic acid quadruplet.

The code provided by he present invention is not entirely rigid; certain choices are provided. For example, positions +1, +5 and +8 may have any amino acid allocation, whilst other positions may have certain options: for example, the present rules provide that, for binding to a central T residue, any one of Ala, Ser or Val may be used at +3. In its broadest sense, therefore, the present invention provides a very large number of proteins which are capable of binding to every defined target nucleic acid quadruplet.

Preferably, however, the number of possibilities may be significantly reduced. For example, the non-critical residues +1, +5 and +8 may be occupied by the residues Lys, Thr and Gln respectively as a default option. In the case of the other choices, for example, the first-given option may be employed as a default. Thus, the code according to the present invention allows the design of a single, defined polypeptide (a "default" polypeptide) which will bind to its target quadruplet.

In a further aspect of the present invention, there is provided a method for preparing a nucleic acid binding protein of the Cys2-His2 zinc finger class capable of binding to a target nucleic acid sequence, comprising the steps of:
 a) selecting a model zinc finger domain from the group consisting of naturally occurring zinc fingers and consensus zinc fingers; and
 b) mutating one or more of positions −1, +2, +3 and +6 of the finger as required according to the rules set forth above.

In general, naturally occurring zinc fingers may be selected from those fingers for which the nucleic acid binding specificity is known. For example, these may be the fingers for which a crystal structure has been resolved: namely Zif 268 (Elrod-Erickson et at., (1996) Structure 4:1171–1180), GLI (Pavletich and Pabo, (1993) Science 261:1701–1707), Tramtrack (Fairall et al., (1993) Nature 366:483–487) and YY1 (Houbaviy et al., (1996) PNAS (USA) 93:13577–13582).

The naturally occurring zinc finger 2 in Zif 268 makes an excellent staning-point from which to engineer a zinc finger and is preferred.

Consensus zinc finger structures may be prepared by comparing the sequences of known zinc fingers, irrespective of whether their binding domain is known. Preferably, the consensus structure is selected from the group consisting of the consensus structure (SEQ ID NO: 6) P Y K C P E C G K S F S Q K S D L V K H Q R T H T G (SEQ ID NO: 5), and the consensus structure (SEQ ID NO: 7) P Y K C S E C G K A F S Q K S N L T R H Q R I H T G E K P (SEQ ID NO: 6).

The consensuses are derived from the consensus provided by Krizek et al., (1991) J. Am. Chem. Soc. 113:4518–4523 and from Jacobs, (1993) PhD thesis, University of Cambridge, UK. In both cases, the linker sequences described above for joining two zinc finger motifs together, namely TGEK (SEQ ID NO: 4) or TGEKP (SEQ ID NO: 5) can be formed on the ends of the consensus. Thus, a P may be removed where necessary, or, in the case of the consensus terminating T G, E K (P) can be added.

When the nucleic acid specificity of the model finger selected is known, the mutation of the finger in order to modify its specificity to bind to the target nucleic acid may be directed to residues known to affect binding to bases at which the natural and desired targets differ. Otherwise, mutation of the model fingers should be concentrated upon residues −1, +2, +3 and +6 as provided for in the foregoing rules.

In order to produce a binding protein having improved binding, moreover, the rules provided by the present invention may be supplemented by physical or virtual modelling of the protein/nucleic acid interface in order to assist in residue selection.

Zinc finger binding motifs designed according to the invention may be combined into nucleic acid binding proteins having a multiplicity of zinc fingers. Preferably, the proteins have at least two zinc fingers. In nature, zinc finger binding proteins commonly have at least three zinc fingers, although two-zinc finger proteins such as Tramtrack are known. The presence of at least three zinc fingers is preferred. Binding proteins may be constructed by joining the required fingers end to end. N-terminus to C-terminus. Preferably, this is effected by joining together the relevant nucleic acid coding sequences encoding the zinc fingers to produce a composite coding sequence encoding the entire binding protein. The invention therefore provides a method for producing a nucleic acid binding protein as defined above, wherein the nucleic acid binding protein is constructed by recombinant DNA technology, the method comprising the steps of:
 a) preparing a nucleic acid coding sequence encoding two or more zinc finger binding motifs as defined above, placed N-terminus to C-terminus;
 b) inserting the nucleic acid sequence into a suitable expression vector; and
 c) expressing the nucleic acid sequence in a host organism in order to obtain the nucleic acid binding protein.

A "leader" peptide may be added to the N-terminal finger. Preferably, the leader peptide is (SEQ ID NO: 8) MAEEKP.

The nucleic acid encoding the nucleic acid binding protein according to the invention can be incorporated into vectors for further manipulation. As used herein, vector (or plasmid) refers to discrete elements that are used to introduce heterologous nucleic acid into cells for either expression or replication thereof. Selection and use of such vehicles are well within the skill of the person of ordinary skill in the art. Many vectors are available, and selection of appropriate vector will depend on the intended use of the vector, i.e. whether it is to be used for DNA amplification or for nucleic acid expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the $2\mu$ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in E. coli and then the same vector is transfected into yeast or mammalian cells even though it is not capable of replicating independently of the host cell chromosome. DNA may also be replicated by insertion into the host genome. However, the recovery of genomic DNA encoding the nucleic acid binding protein is more complex than that of exogenously replicated vector because restriction enzyme digestion is required to excise nucleic acid binding protein DNA. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript® vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up nucleic acid binding protein nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes the nucleic acid binding protein. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to nucleic acid binding protein encoding nucleic acid. Such a promoter may be inducible or constitutive. The promoters are operably linked to DNA encoding the nucleic acid binding protein by removing the promoter from the source DNA by restriction enzyme digestion and inserting the isolated promoter sequence into the vector. Both the native nucleic acid binding protein promoter sequence and many heterologous promoters may be used to direct amplification and/or expression of nucleic acid binding protein encoding DNA.

Promoters suitable for use with prokaryotic hosts include, for example, the β-lactamase and lactose promoter systems, alkaline phosphatase, the tryptophan (Trp) promoter system and hybrid promoters such as the Eac promoter. Their nucleotide sequences have been published, thereby enabling the skilled worker operably to ligate them to DNA encoding nucleic acid binding protein, using linkers or adapters to supply any required restriction sites. Promoters for use in bacterial systems will also generally contain a Shine-Delgarno sequence operably linked to the DNA encoding the nucleic acid binding protein.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60–89, 1990). In the *E. coli* BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for overproduction of many proteins. Alternatively the polymerase gene may be introduced on a lambda phage by infection with an int- phage such as the CE6 phage which is commercially available (Novagen, Madison, USA), other vectors include vectors containing the lambda PL promoter such as PLEX (Invitrogen, NL), vectors containing the trc promoters such as pTrcHisXpressTm (Invitrogen) or pTrc99 (Pharmacia Biotech, SE) or vectors containing the tac promoter such as pKK223-3 (Pharmacia Biotech) or PMAL (New England Biolabs, MA, USA).

Moreover, the nucleic acid binding protein gene according to the invention preferably includes a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

Nucleic acid binding protein gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the acting promoter or a very strong promoter, e.g. a ribosomal protein promoter, and from the promoter normally associated with nucleic acid binding protein sequence, provided such promoters are compatible with the host cell systems.

Transcription of a DNA encoding nucleic acid binding protein by higher eukaryotes may be increased by inserting an enhancer sequence into the vector. Enhancers are relatively orientation and position independent. Many enhancer sequences are known from mammalian genes (e.g. elastase and elobin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to nucleic acid binding protein DNA. but is preferably located at a site 5' from the promoter.

Advantageously, a eukaryotic expression vector encoding a nucleic acid binding protein according to the invention may comprise a locus control region (LCR). LCRs are capable of directing high-level integration site independent expression of transgenes integrated into host cell chromatin, which is of importance especially where the nucleic acid binding protein gene is to be expressed in the context of a permanently-transfected eukaryotic cell line in which chromosomal integration of the vector has occurred, or in transgenic animals.

Eukaryotic vectors may also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of tie mRNA encoding nucleic acid binding protein.

An expression vector includes any vector capable of expressing nucleic acid binding protein nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding nucleic acid binding protein may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding nucleic acid binding protein in mammalian cells. Transient expression usually involves the use of an expression vector that is able to replicate efficiently in a host cell, such that the host cell accumulates many copies of the expression vector, and, in turn, synthesises high levels of nucleic acid binding protein. For the purposes of the present invention, transient expression systems are useful e.g. for identifying nucleic acid binding protein mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing nucleic acid binding protein expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing the nucleic acid binding protein. Suitable prokaryotes include eubacteria, such as Gram-negative or Gram-positive organisms, such as *E. coli*; e.g. *E. coli* K-12 strains. DH5a and-HB101. or Bacilli. Further hosts suitable for the nucleic acid binding protein encoding vectors include eukaryotic microbes such as filamentous fungi or yeast, e.g. *Saccharomyces cerevisiae*. Higher eukaryotic cells include insect and vertebrate cells, particularly mammalian cells including human cells or nucleated cells from other multicellular organisms. In recent years propagation of vertebrate cells in culture (tissue culture) has become a routine procedure. Examples of useful mammalian host cell lines are epithelial or fibroblastic cell lines such as Chinese hamster ovary (CHO) cells. NIH 3T3 cells. HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of the nucleic acid binding protein-encoding nucleic acid to form the nucleic acid binding protein. The precise amounts of DNA encoding the nucleic acid binding protein may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heteroloeous DNA by the calcium phosphate coprecipitation technique or by electroporation. Numerous methods of transfection are known to the skilled worker in the field. Successful transfection is generally recognised when any indication of the operation of thisvector-occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see. e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby the nucleic acid binding protein encoded by the DNA is expressed. The composition of suitable media is known to those in the art, so that they can be readily prepared. Suitable culturing media are also commercially available.

In a further aspect, the invention also provides means by which the binding of the protein designed according to the rules can be improved by randomising the proteins and selecting for improved binding. In this aspect, the present invention represents an improvement of the method set forth in WO 96/06166. Thus, zinc finger molecules designed according to the invention may be subjected to limited randomisation and subsequent selection, such as by phage display, in order to optimise the binding characteristics of the molecule.

Preferably, therefore, the method according to the invention comprises the further steps of randomising the sequence of the zinc finger binding motifs at selected sites, screening the randomised molecules obtained and selecting the molecules having the most advantageous properties. Generally, those molecules showing higher affinity and/or specificity of the target nucleic acid sequence are selected.

Mutagenesis and screening of target nucleic acid molecules may be achieved by any suitable means. Preferably, the mutagenesis is performed at the nucleic acid level, for example by synthesising novel genes encoding mutant proteins and expressing these to obtain a variety of different proteins. Alternatively, existing genes can be themselves mutated, such by site-directed or random mutagenesis, in order to obtain the desired mutant genes.

Mutations may be performed by any method known to those of skill in the art. Preferred, however, is site-directed mutagenesis of a nucleic acid sequence encoding the protein of interest. A number of methods for site-directed mutagenesis are known in the art, from methods employing single-stranded phage such as M13 to PCR-based techniques (see "PCR Protocols: A guide to methods and applications", M. A. Innis. D. H. Gelfand, J. J. Sninsky, T. J. White (eds.). Academic Press. New York, 1990). Preferably, the commercially available Altered Site II Mutagenesis System (Promega) may be employed, according to the directions given by the manufacturer.

Screening of the proteins produced by mutant genes is preferably performed by expressing the genes and assaying the binding ability of the protein product. A simple and advantageously rapid method by which this may be accomplished is by phage display, in which the mutant polypeptides are expressed as fusion proteins with the coat proteins of filamentous bacteriophage, such as the minor coat protein pH of bacteriophage m13 or gene III of bacteriophage Fd, and displayed on the capsid of bacteriophage transformed with the mutant genes. The target nucleic acid sequence is used as a probe to bind directly to the protein on the phage surface and select the phage possessing advantageous mutants, by affinity purification. The phage are then amplified by passage through a bacterial host, and subjected to further rounds of selection and amplification in order to enrich the mutant pool for the desired phage and eventually isolate the preferred clone(s). Detailed methodology for phage display is known in the art and set forth, for example, in U.S. Pat. No. 5,223,409; Choo and Klug, (1995) Current Opinions in Biotechnology 6:431–436; Smith, (1985) Science 228:1315–1317; and McCafferty et al., (1990) Nature 348:552–554; all incorporated herein by reference. Vector systems and kits for phage display are available commercially, for example from Pharmacia.

Randomisation of the zinc finger binding motifs produced according to the invention is preferably directed to those residues where the code provided herein gives a choice of residues. For example, therefore, positions +1, +5 and +8 are advantageously randomised, whilst preferably avoiding hydrophobic amino acids; positions involved in binding to the nucleic acid, notably −1, +2, +3 and +6, may be randomised also, preferably within the choices provided by the rules of the present invention.

Preferably, therefore, the "default" protein produced according to the rules provided by the invention can be improved by subjecting the protein to one or more rounds of randomisation and selection within the specified parameters.

Advantageously, the zinc finger proteins according to the invention may be randomised such that 2 or more residues are randomised together. For example, it is preferred that residues −1 and +6 of adjacent zinc fingers in a zinc finger protein be randomised together. Preferably, position +6 of a zinc finger and positions −1, +1, +2 and +3 of an adjacent zinc finger are randomised together. This reflects cooperativity between adjacent zinc fingers, reflected in the binding of positions +2 and +6 of adjacent zinc fingers to the same position on opposite strands of the DNA double helix, and allows every possible triple junction base sequence to be specified.

Nucleic acid binding proteins according to the invention may be employed in a wide variety of applications, including diagnostics and as research tools. Advantageously, they may be employed as diagnostic tools for identifying the presence of nucleic acid molecules in a complex mixture, nucleic acid binding molecules according to the invention can differentiate single base pair changes in target nucleic acid molecules.

Accordingly, the invention provides a method for determining the presence of a target nucleic acid molecule, comprising the steps of:

a) preparing a nucleic acid binding protein by the method set forth above which is specific for the target nucleic acid molecule;

b) exposing a test system comprising the target nucleic acid molecule to the nucleic acid binding protein under conditions which promote binding and removing any nucleic acid binding protein which remains unbound;

c) detecting the presence of the nucleic acid binding protein in the test system.

In a preferred embodiment, the nucleic acid binding molecules of the invention can be incorporated into an ELISA assay. For example, phage displaying the molecules of the invention can be used to detect the presence of the target nucleic acid, and visualised using enzyme-linked anti-phage antibodies.

Further improvements to the use of zinc finger phage for diagnosis can be made, for example, by co-expressing a marker protein fused to the minor coat protein (gVIII) of bacteriophage. Since detection with an anti-phage antibody would then be obsolete, the time and cost of each diagnosis would be further reduced. Depending on the requirements, suitable markers for display might include the fluorescent proteins (A. B. Cubitt, et al., (1995) *Trends Biochem Sci.* 20, 448–455; T. T. Yang, et al., (1996) *Gene* 173, 19–23), or an enzyme such as alkaline phosphatase which has been previously displayed on gIII ( J. McCafferty, R. H. Jackson, D. J. Chiswell, (1991) *Protein Engineering* 4, 955–961) Labelling different types of diagnostic phage with distinct markers would allow multiplex screening of a single nucleic acid sample. Nevertheless, even in the absence of such refinements, the basic ELISA technique is reliable, fast, simple and particularly inexpensive. Moreover it requires no specialised apparatus, nor does it employ hazardous reagents such as radioactive isotopes, making it amenable to routine use in the clinic. The major advantage of the protocol is that it obviates the requirement for gel electrophoresis, and so opens the way to automated nucleic acid diagnosis.

The invention provides nucleic acid binding proteins which can be engineered with exquisite specificity. The invention lends itself, therefore, to the design of any molecule of which specific nucleic acid binding is required. For example, the proteins according to the invention may be employed in the manufacture of chimeric restriction enzymes, in which a nucleic acid cleaving domain is fused to a nucleic acid binding domain comprising a zinc finger as described herein.

Moreover, the invention provides therapeutic agents and methods of therapy involving use of nucleic acid binding proteins as described herein. In particular, the invention provides the use of polypeptide fusions comprising an integrase, such as a viral integrase, and a nucleic acid binding protein according to the invention to target nucleic acid sequences in vivo (Bushman, (1994) PNAS (USA) 91:9233–9237). In gene therapy applications, the method may be applied to the delivery of functional genes into defective genes, or the delivery of nonsense nucleic acid in order to disrupt undesired nucleic acid. Alternatively, genes may be delivered to known, repetitive stretches of nucleic acid, such as centromeres, together with an activating sequence such as an LCR. This would represent a route to the safe and predictable incorporation of nucleic acid into the genome.

In conventional therapeutic applications, nucleic acid binding proteins according to the invention may be used to specifically knock out cell having mutant vital proteins. For example, if cells with mutant ras are targeted, they will be destroyed because ras is essential to cellular survival. Alternatively, the action of transcription factors may be modulated, preferably reduced, by administering to the cell agents which bind to the binding site specific for the transcription factor. For example, the activity of HIV tat may be reduced by binding proteins specific for HIV TAR.

Moreover, binding proteins according to the invention may be coupled to toxic molecules, such as nucleases, which are capable of causing irreversible nucleic acid damage and cell death. Such agents are capable of selectively destroying cells which comprise a mutation in their endogenous nucleic acid.

Nucleic acid binding proteins and derivatives thereof as set forth above may also be applied to the treatment of infections and the like in the form of organism-specific antibiotic or antiviral drugs. In such applications, the binding proteins may be coupled to a nuclease or other nuclear toxin and targeted specifically to the nucleic acids of microorganisms.

The invention likewise relates to pharmaceutical preparations which contain the compounds according to the invention or pharmaceutically acceptable salts thereof as active ingredients, and to processes for their preparation.

The pharmaceutical preparations according to the invention which contain the compound according to the invention or pharmaceutically acceptable salts thereof are those for enteral, such as oral, furthermore rectal, and parenteral administration to (a) warm-blooded animal(s), the pharmacological active ingredient being present on its own or together with a pharmaceutically acceptable carrier. The daily dose of the active ingredient depends on the age and the individual condition and also on the manner of administration.

The novel pharmaceutical preparations contain, for example, from about 10% to about 80%, preferably from about 20% to about 60%, of the active ingredient. Pharmaceutical preparations according to the invention for enteral or parenteral administration are, for example, those in unit dose forms, such as sugar-coated tablets, tablets, capsules or suppositories, and furthermore ampoules. These are prepared in a manner known per se, for example by means of conventional mixing, granulating, sugar-coating, dissolving or lyophilising processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

Suitable carriers are, in particular, fillers, such as sugars, for example lactose, sucrose, mannitol or sorbitol, cellulose preparations and/or calcium phosphates, for example tricalcium phosphate or calcium hydrogen phosphate, furthermore binders, such as starch paste, using, for example, corn, wheat, rice or potato starch, gelatin, tragacanth, methylcellulose and/or polyvinylpyrrolidone, if desired, disintegrants, such as the abovementioned starches, furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate, and/or polyethylene glycol. Sugar-coated tablet cores are provided with suitable coatings which, if desired, are resistant to gastric juice, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropylmethylcellulose phthalate. Colorants or pigments, for example to identify or to indicate different doses of active ingredient, may be added to the tablets or sugar-coated tablet coatings.

Other orally utilisable pharmaceutical preparations are hard gelatin capsules, and also soft closed capsules made of gelatin and a plasticiser, such as glycerol or sorbitol. The hard gelatin capsules may contain the active ingredient in the form of granules, for example in a mixture with fillers, such as lactose, binders, such as starches, and/or lubricants, such as talc or magnesium stearate, and, if desired, stabilisers. In soft capsules, the active ingredient is preferably dissolved or suspended in suitable liquids, such as fatty oils, paraffin oil or liquid polyethylene glycols, it also being possible to add stabilisers.

Suitable rectally utilisable pharmaceutical preparations are, for example, suppositories, which consist of a combination of the active ingredient with a suppository base.

Suitable suppository bases are, for example, natural or synthetic triglycerides, paraffin hydrocarbons, polyethylene glycols or higher alkanols. Furthermore, gelatin rectal capsules which contain a combination of the active ingredient with a base substance may also be used. Suitable base substances are, for example, liquid triglycerides, polyethylene glycols or paraffin hydrocarbons.

Suitable preparations for parenteral administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, if necessary, also stabilisers.

The dose of the active ingredient depends on the warm-blooded animal species, the age and the individual condition and on the manner of administration. In the normal case, an approximate daily dose of about 10 mg to about 250 mg is to be estimated in the case of oral administration for a patient weighing approximately 75 kg.

The invention is described below, for the purpose of illustration only, in the following examples.

EXAMPLE 1

Determination of Binding Site Preferences in Zinc Fingers

Design of Zinc Finger Phage Display Libraries

Zinc finger-DNA recognition at the interface between adjacent DNA subsites is studied using a zinc finger phage display library. This library is based on the three-finger DNA-binding domain of Zif268, but contains randomisations of amino acids from finger 2 (F2) and finger 3 (F3), at residue positions which could form a network of contacts across the interface of their DNA subsites. The detailed design of the library is shown in FIG. 1c, together with the generic DNA binding site used in selections. Briefly, the library contains randomisations at F2 residue position 6 (hereafter denoted F2[+6]) and F3 residue positions −1, +1, +2 and +3 (hereafter denoted F3[−1], F3[+2], etc).

Library selections are carried out using DNA binding sites that resembled the Zif268 operator, but which contained systematic combinations of bases in the DNA doublet which forms the base-step between of F2 and F3. DNA binding sites are of the generic form 5'-GNX-XCG-GCG-3' (SEQ ID NO:7), where X—X denotes a given combination of the bases at the interface between the DNA subsites, and N denotes that the four bases are equally represented at DNA position 3. Thus the interaction between F3[+3] and nucleotide position 3N is allowed complete freedom in this experiment. This feature of the library allows selection of a large family (or database) of related zinc fingers that bind a given combination of bases at nucleotide positions 4X and 5X, but which are non-identical owing to different interactions with the middle base in the nominal triplet subsite of F3.

The first library to be constructed, LIB-A, contains randomisations at F2 residue position 6 and F3 residue positions −1, 1, 2 and 3 (see FIG. 2), and is sorted using the DNA sequence 5'GNX-XCG-GCG-3' (SEQ ID NO:8), where X—X denotes a known combination of the two bases at DNA positions 4X and 5X, and N denotes an equal probability of any of the four bases at DNA position 3. The second library, LIB-B, contains randomisations at F2 residue position 6 and F3 residue positions −1 and 2, and is sorted using the DNA sequence 5'-GCX-XCG-GCG3', where X—X denotes a known combination of the two bases at DNA positions 4X and 5X.

The genes for the two different zinc finger phage display libraries are assembled from four synthetic DNA oligonucleotides by directional end-to-end ligation using three short complementary DNA linkers. The oligonucleotides contain selectively randomised codons (of sequence NNS; N=A/C/G/T, S=G/C) in the appropriate amino acid positions of fingers 2 and 3. The constructs are amplified by PCR using primers containing Not I and Sfi I restriction sites, digested with the above endonucleases to produce cloning overhangs, and ligated into phage vector Fd-Tet-SN. Electrocompetent E. coli TG 1 cells are transformed with the recombinant vector and plated onto TYE medium (1.5% agar, 1% Bacto tryptone, 0.5% Bacto yeast extract, 0.8% NaCl) containing 15 µg/ml tetracycline.

Allowing this freedom to some protein-DNA interactions that are not being studied is a useful strategy towards increasing the diversity of clones which can be obtained from any one selection experiment. However, at the same time, it is important to limit the number of contacts that are allowed contextual freedom at any one time, otherwise there is a dancer that a subset of particularly strong intermolecular interactions will dominate the selections. Anticipating this eventuality, a smaller sublibrary is also created that contains randomised residues only in positions F2[+6] and F3[−1 and +2], and therefore does not allow for contextual freedom in selections. Clones selected from this library are marked with an asterisk when they are discussed herein.

Experimental Strategy

Phage selections from the two zinc finger libraries are performed separately in order to determine the diversity of DNA sequences which can be bound specifically by members of each library. Sixteen selections are performed on each library, using the different DNA binding sites that correspond to all 16 possible combinations of bases at nucleotide positions 4X and 5X. The DNA binding site used to select specifically binding phage is immobilized on a solid surface, while a 10fold excess of each of the other 15 DNA sites is present in solution as a specific competitor.

Phage Selections

Tetracycline resistant colonies are transferred from plates into 2×TY medium (16 g/litre Bacto tryptone, 10 g/litre Bacto yeast extract, 5 g/litre NaCl) containing 50 µM $ZnCl_2$ and 15 µg/ml tetracycline, and cultured overnight at 30° C. in a shaking incubator. Cleared culture supernatant containing phage particles is obtained by centrifuging at 300 g for 5 minutes.

Biotinylated DNA target sites (1 pmol) are bound to streptavidin-coated tubes (Boehringer Mannheim). Phage supernatant solutions are diluted 1:10 in PBS selection buffer (PBS containing 50 µM $ZnCl_2$, 2% Marvel, 1% Tween, 20 µg/ml sonicated salmon sperm DNA, 10 pmol/ml of each of the 15 other possible unbiotinylated DNA sites), and 1 ml is applied to each tube for 1 hour at 20° C. After this time, the tubes are emptied and washed 20 times with PBS containing 5 µM $ZnCl_2$, 2% Marvel and 1% Tween. Retained phage are eluted in 0.1 ml 0.1M triethylamine and neutralised with an equal volume of 1M Tris (pH 7.4). Logarithmic-phase E. coli TG 1 (0.5 ml) are infected with eluted phage (50 µl), and used to prepare phase supernatants for subsequent rounds of selection. After 3 rounds of selection, E. coli infected with selected phage are plated, individual colonies are picked and used to grow phage for binding site signature assays and DNA sequencing.

After three rounds of phage selection against a particular DNA binding site. individual zinc finger clones are recovered, and the DNA binding specificity of each clone is determined by the binding site signature method. This involves screening each zinc finger phase for binding to eight different libraries of the DNA binding site, designed such that each library contains one fixed base and one randomised base at either of positions 4X and 5X (i.e. libraries GN, AN, TN, CN, and NG, NA, NT, NC). Thus each of the 16 DNA binding sites used in selection experiments is specified by a unique combination of two libraries—for example, the DNA binding site containing 4G5G is present in only two of the eight libraries in which the relevant doublet had one nucleotide randomised and the other nucleotide fixed as guanine, i.e. libraries 4G5N and 4N5G. The eight DNA libraries used in binding site signatures are arrayed across a microtitre plate and zinc finger phase binding is detected by phage ELISA. The pattern of binding to the eight DNA libraries reveals the DNA sequence specificity (or preference) of each phage clone, and only those clones found to be relatively specific are subsequently sequenced to reveal the identity of the amino acids present in the randomised zinc finger residue positions.

Procedures are as described previously (Choo, Y. & Klug. A. (1994) Proc. Natl. Acad. Sci. USA 91, 11163–11167; Choo, Y. & Klug. A. (1994) Proc. Natl. Acad. Sci. USA 91, 11168–11172). Briefly, 5'-biotinylated positionally randomised oligonucleotide libraries, containing Zif268 operator variants, are synthesised by primer extension as described. DNA libraries (0.4 pmol/well for LIB-A and 1.2 pmol/well, for LIB-B) are added to streptavidin-coated ELISA wells (Boehringer-Mannheim) in PBS containing 50 µM $ZnCl_2$ (PBS/Zn). Phage solution (overnight bacterial culture supernatant diluted 1:10 in PBS/Zn containing 2% Marvel, 1% Tween and 20 µg/ml sonicated salmon sperm DNA) are applied to each well (50 µl/well). Binding is allowed to proceed for one hour at 20° C. Unbound phage are removed by washing 6 times with PBS/Zn containing 1% Tween, then 3 times with PBS/Zn. Bound phage are detected by ELISA using horseradish peroxidase-conjugated anti-M13 IgG (Pharmacia Biotech) and the colourimetric signal quantitated using SOFFMAX 2.32 (Molecular Devices).

The coding sequence of individual zinc finger clones is amplified by PCR using external lilt primers complementary to phage sequence. These PCR products are sequenced manually using Thermo Sequenase cycle sequencing (Amersham Life Science).

Analysis of Phage-Selected Zinc Fingers

Figure 3:
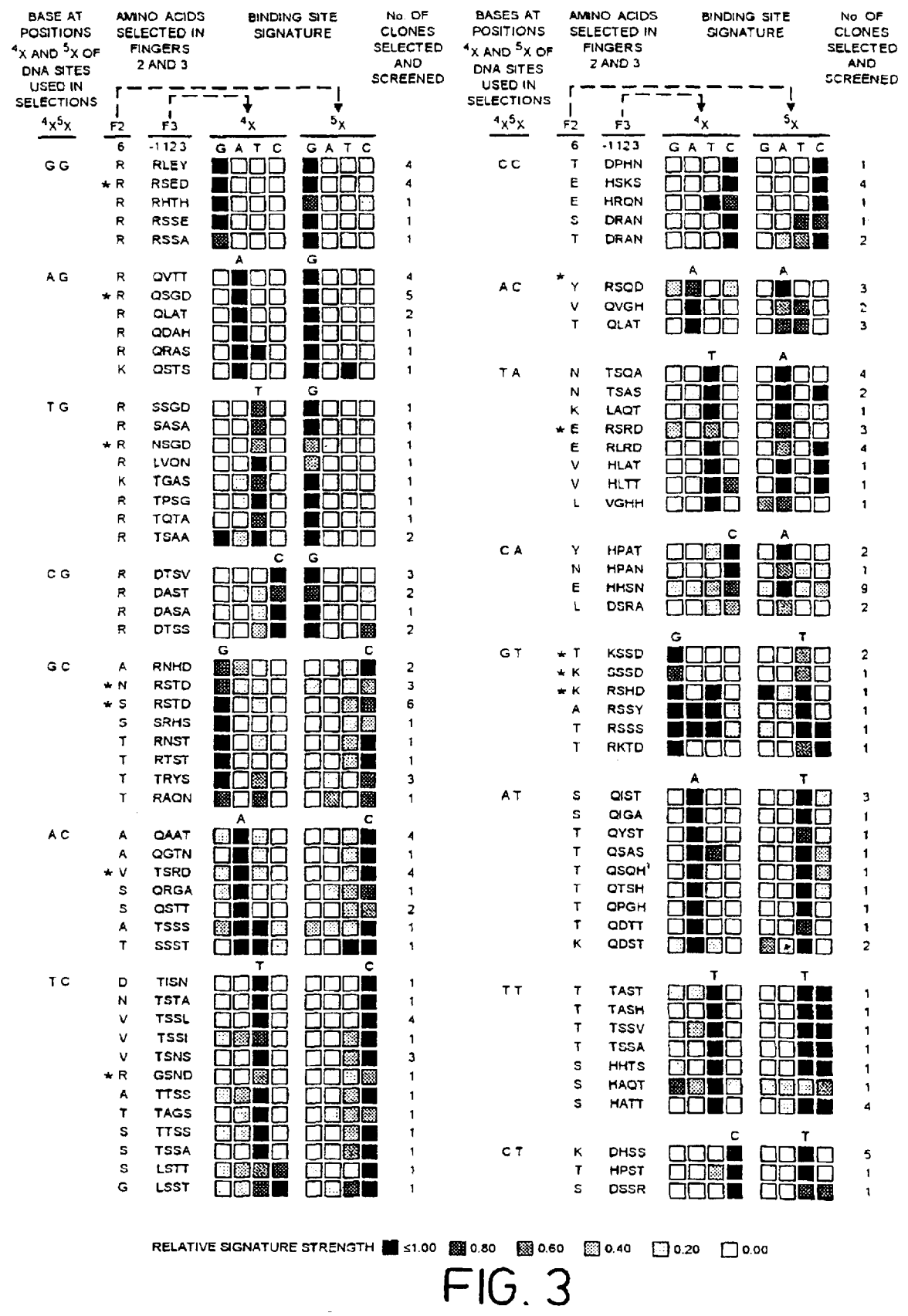
Figure 4:
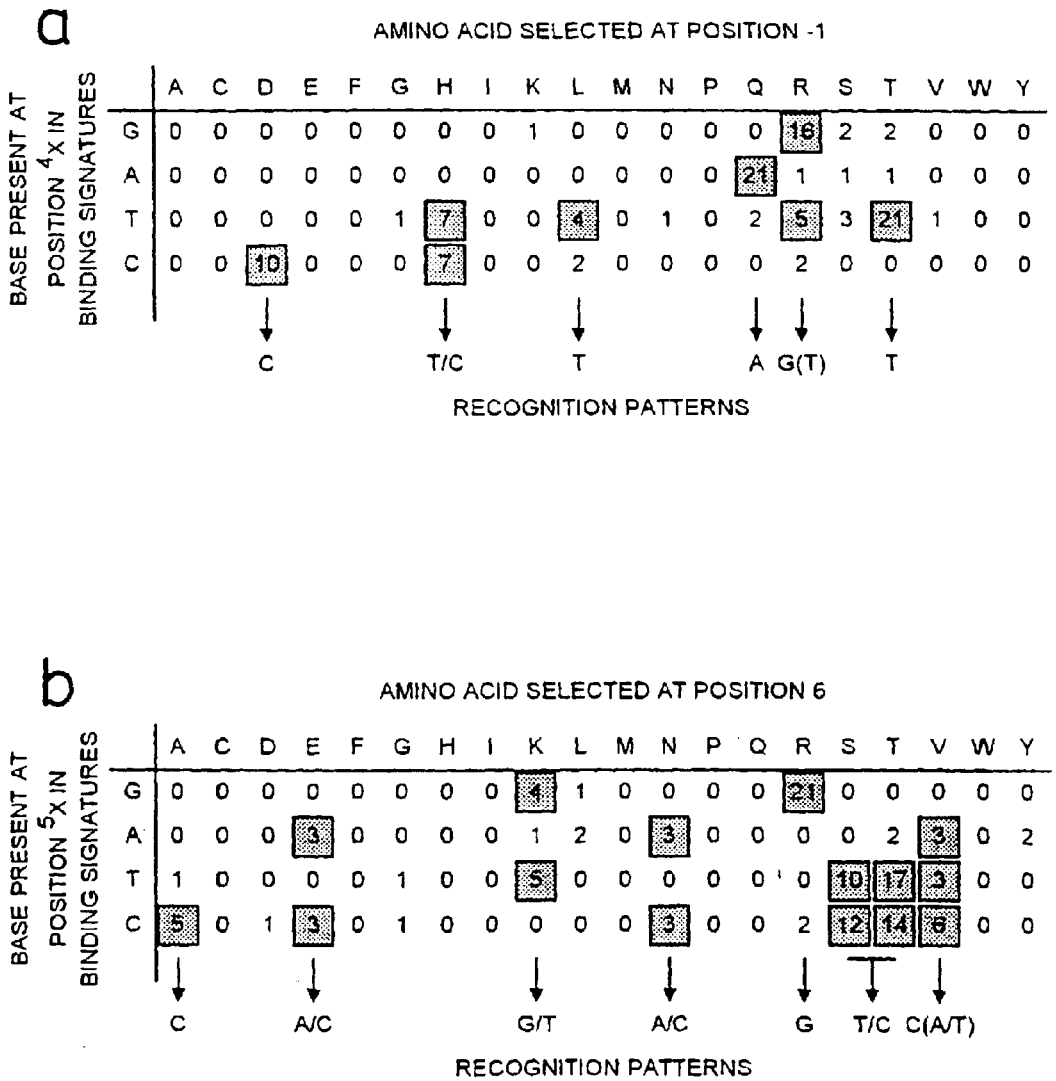
FIG. 4 shows the base/amino acid correlation of the clones isolated from phase selections. Recognition patterns are highlighted.

FIG. 3 shows the binding site signatures of relatively sequence-specific zinc finger phages selected from both libraries, using the 16 different DNA doublets which form the base-step between the DNA subsites of fingers 2 and 3. The results show that zinc finger clones are selected which bind specifically to almost all subsites, including those triplets in which the 5' position (nucleotide 5X in the model system) is fixed as a base other than guanine. Overall, the selections show that any of the four bases can be bound specifically in both the 5' and 3' positions of a nominal triplet subsite. The results are summarized in FIG. 4.

Selections from the smaller sub-library yield fingers that can bind specifically to only 8 of the 16 doublets, whereas members of the larger library yield fingers that recognise 15 out of the 16 doublets. It is not known whether this difference in efficacy originates from the inclusion of more randomised positions in the larger library, or the conformational flexibility afforded by the contextual freedom designed into the larger library, or both. The only base-step that does not yield specific zinc fingers is 4G5A. This dinucleotide may induce an unfavourable DNA deformation in the context of the DNA binding sites used for selection.

EXAMPLE 2

Determination of +2 Specificity for Position 1

The amino acid present in α-helical position 2 of a zinc finger can help determine the specificity for the base-pair at the interface of two overlapping DNA quadruplet subsites (see FIG. 1B; position 5/5', corresponding to position 1 or 4 of the quadruplet as discussed above). An Asp residue present in F3[+2] of wild-type Zif268 has been shown to play a role in DNA recognition, and further examples are generated by the current phage display experiments (See Example 1 for details, and FIG. 5A).

Figure 5:
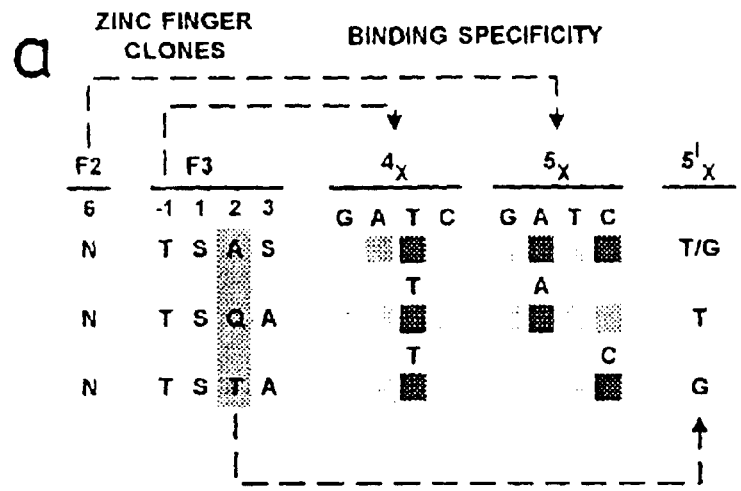
FIG. 5, illustrates the sequence-specific interactions selected for at position 2 of the α-helix, binding to position 1 of the quadruplet (SEQ ID NOS: 74, 73, 54, 15–16, 57–58, 70, 73, 75, 45, 67, 105, 84, 76, 77, 48, 38 41 and 65–66, respectively, in order of appearance).

The experimental protocol followed is that of Example 1. FIG. 5A shows an example of related zinc finger clones showing the effect of α-helical position 2 on DNA-binding specificity. In this case, position 6 of finger 2 is invariant (Asn) and the change in case specificity in the zinc finger in order to select for contact to this base is dictated by position +2 in finger 3.

This family of zinc fingers is derived from selections using DNA binding sites containing 4T5A or 4T5C subsite interfaces. The base preference for the 5X- 5'X base-pair is determined by the amino acid present at F3[+2], probably by the formation of cross-strand contacts.

FIG. 5B shows examples of correlations between certain amino acids selected at F3[+2] and the identity of the base present at position 5'X. Selections reveal the possibility of DNA contacts from five amino acids (Asn, Gln, Arg, Lys and His) which are all capable of donating a H-bond to the exocyclic oxygen atom of either guanine ($O_6$) or thymine ($O_4$) in nucleotide position 5'X. The clones isolated with these amino acids at F3[+2] are listed in this diagram together with the binding site signature showing the base-preference at position 5'X. Overall, Ser dominated the selections with an occurrence of 38%. in accord with its presence in position 2 in over half of all known zinc fingers. Threonine, Ala and Gly occurred frequently in the selections (15%, 15% and 9% respectively) but did not show any discernible patterns of discrimination. Certain amino acids (Cys. Asp, Phe, lle, Leu, Met, Pro, Val and Trp) are never selected in position 2. Their ability to bind in certain situations is however not to be excluded.

A small subset of amino acids selected in F3[+2] show significant correlations to the identity of the base-pair in position 5'X (FIG. 5B), suggesting that cross-strand interactions between these may be a general mechanism of DNA-recoznition. Most of these correlations can be rationalised as pairings between hydrogen bond donors in F3[+2] and guanine or thymine in DNA position 5'X, in accordance with the framework of the Zif268 model, in contrast to amino acids that are never selected in position 2, or amino acids that are selected but which show no significant correlations, the amino acids which consistently appear to play a role in DNA recognition from this position have side chains with multiple hydrogen bonding groups. It is possible that these residues can play a role in base recognition because they achieve greater specificity by participating in buttressing networks.

EXAMPLE 3

Construction of a Zinc Finger Protein

The target selected for the zinc finger nucleic acid binding protein is the activating point mutation of the human EJ bladder carcinoma ras oncogene, which was the first DNA lesion reported to confer transforming properties on a cellular proto-oncogene. Since the original discovery, ras gene mutations have been found to occur at high frequencies in a variety of human cancers and are established targets for the diagnosis of oncogenesis at early stages of tumour growth.

Figure 6B:
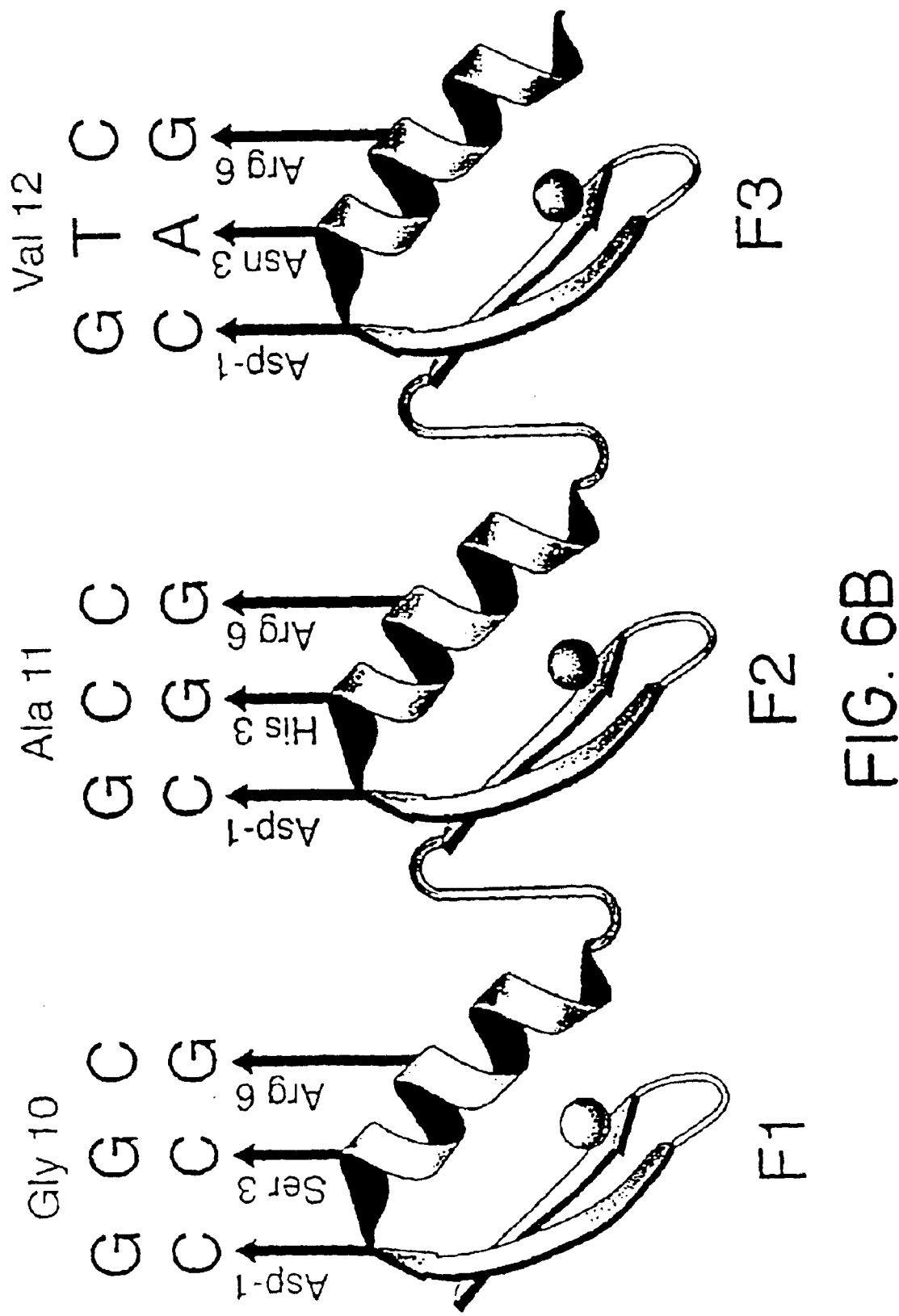
FIG. 6 illustrates the design of a zinc finger binding protein (SEQ ID NOS: 110–114, respectively, in order of appearance) specific for a G12V mutant ras oncogene.

The EJ bladder carcinoma mutation is a single nucleotide chance in codon 12 of H-ras, which results in a mutation from GGC to GTC at this position. A zinc finger peptide is designed to bind a 10 bp DNA site assigned in the noncoding strand of the mutant ras gene, such that three fingers contact 'anticodons' 10, 11 and 12 in series, as shown in FIG. 6, plus the 5' preceding G (on the + strand of the DNA). The rationale of this assignment takes into account the fact that zinc fingers make most contacts to one DNA strand, and the mutant noncoding strand carries an adenine which can be strongly discriminated from the cytosine present in the wild-type ras, by a bidentate contact from an asparagine residue.

The first finger of the designer lead peptide is designed according to the rules set forth herein starting from a Zif268 finger 2 model to bind the quadruplet 5'-GCCG-3', which corresponds to 'anticodon' 10 of the designated binding site plus one 3' base. The finger has the following sequence (SEQ ID NO: 9):

```
F Q C R I C M R N F S D R S S L T R H T R T R T H T G E K
P
            -1 1 2 3 4 5 6 7 8 9
```

A DNA coding sequence encoding this polypeptide is constructed from synthesised oligonucleotides.

Given the similarity of the DNA subsites, the second and third fingers of the DNA-binding domain are direct repeats of this first finger, but in which the third α-helical residue which contacts base 3 of a quadruplet, +3, is mutated according to recognition rules, to histidine in finger 2 and asparagine in finger 3, such that the specificity of these fingers is predicted to be 5'-GGCG-3' (includes 'anticodon' 11) and 5'-GACG-3' (includes 'anticodon' 12) respectively. Thus the second and third finger polypeptides have the sequences SEQ ID NOS: 10 and 11, respectively)

```
F Q C R I C M R N F S D R S H L T R H T R T H T G E K P
``` and (SEQ ID NO: 12)

```
F Q C R I C M R N F S D R S N L T R H T R T R T G E K
``` respectively.

A construct consisting of DNA sequences encoding the three fingers joined together, preceded by a leader MAEEKP (SEQ ID NO: 8) at the N-terminus, is cloned as a fusion to the minor coat protein (gene III) of bacteriophage Fd in the phage vector Fd-Tet-SN (Y. Choo, A. Klug, (1994) *Proc. Natl. Acad. Sci. U.S.A.* 91, 11163–11167). In phage display screening $K_d$ of 17nM, and to discriminate strongly against the wild-type sequence.

EXAMPLE 4

Improvement of Binding Performance by Selective Randomisation

While a $K_d$ of 17 nM is sufficient for most practical applications of DNA-binding proteins, the apparent affinity of the designed protein falls about 5-fold short of the $K_d$s in the nanomolar range which are found for the reaction of wild-type zinc finger proteins with their natural binding sites (Y. Choo, A. Klug, (1994) *Proc. Natl. Acad. Sci. U.S.A.* 91, 11168–11172).

According to the recognition rules, the first finger of the lead peptide could contact cytosine using one of Ser, Asp, Glu, Leu, Thr or Val in the third α-helix position. To determine the optimal contact, the codon for helical position 3 of finger 1 is engineered by cassette mutagenesis to have position 1=A/G, position 2=A/C/G and position 3=C/G. Therefore in addition to Asp, Glu, Ser and Thr, the randomisation also specifies Ala, Arg, Asn, Gly and Lys. Selections from this mini-library are over one round of phage binding to 5 nM mutant DNA oligo in 100 μl PBS containing 50 μM $ZnCl_2$, 2% (w/v) fat-free dried milk (Marvel) and 1% (v/v) Tween-20, with 1 μg poly dIdC as competitor, followed by six washes with PBS containing 50 μM $ZnCl_2$ and 1% (v/v) Tween-20. Bound phage are eluted with 0.1M triethylamine for 3 mins, and immediately transferred to an equal volume of 1M Tris-Cl pH 7.4.

A single round of randomisation and selection is found to be sufficient to improve the affinity of the lead zinc finger peptide to this standard. A small library of mutants is constructed with limited variations specifically in the third α-helical position (+3) of finger 1 of the designed peptide.

Figure 7:
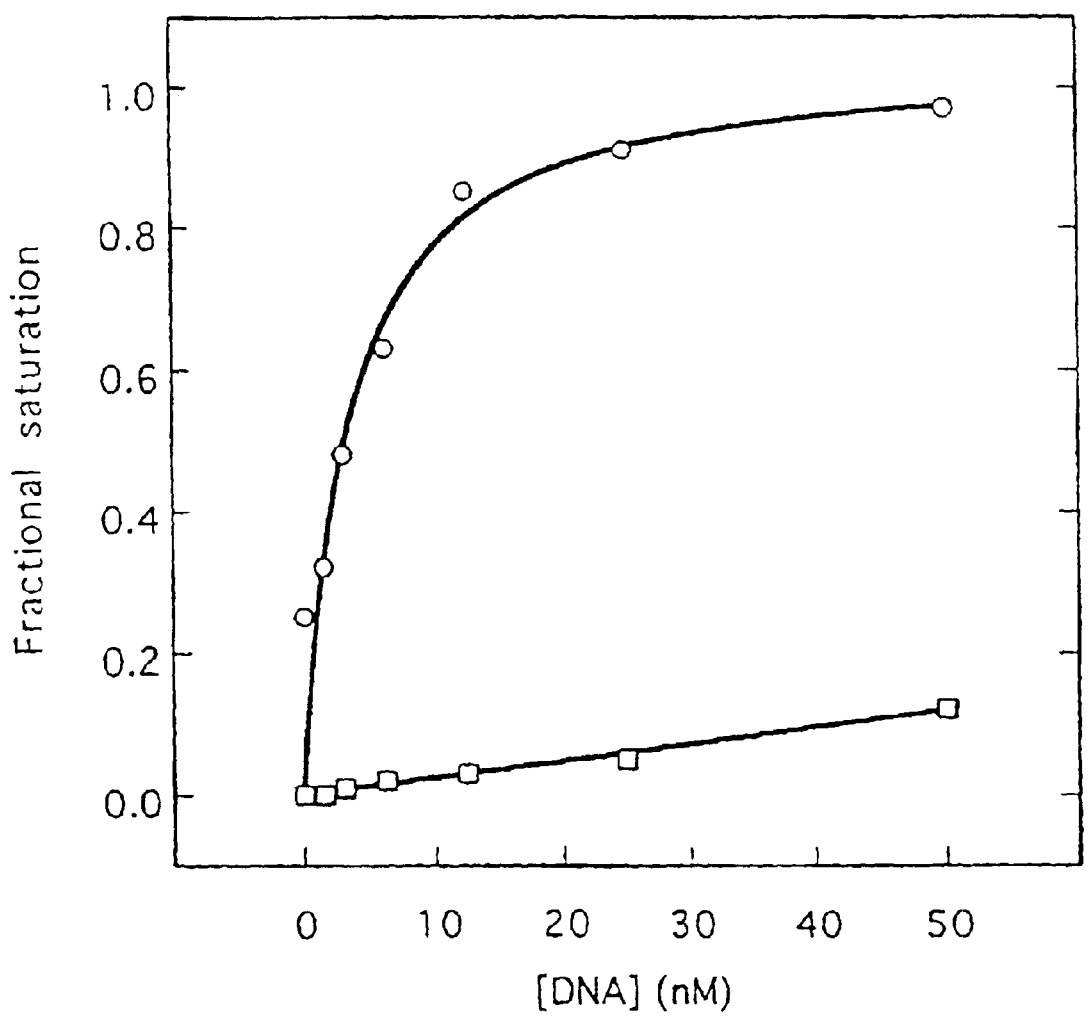
FIG. 7 illustrates the binding specificity of the binding protein for the oncogene as opposed to the wild-type ras sequence.

Selection from this library yields an optimised DNA-binding domain with asparagine at the variable position, which is able to bind the mutant ras sequence with an apparent $K_d$ of 3 nM, i.e. equal to that of the wild-type Zif268 DNA-binding domain (FIG. 7) The selection of asparagine at this position to bind opposite a cytosine is an unexpected deviation from the recognition rules, which normally pair asparagine with adenine.

The selection of asparagine is, however, consistent with physical considerations of the protein-DNA interface. In addition to the classical bidentate interaction of asparagine and adenine observed in zinc finger-DNA complexes, asparazine has been observed to bridge a base-pair step in the major groove of DNA, for example in the co-crystal structures of the GCN4 DNA-binding domain. A number of different base-pair steps provide the correct stereochemical pairings of hydrogen bond donors and acceptors which could satisfy asparagine, including the underlined step G<u>CC</u> of ras 'anticodon' 10. Although asparagine in position 3 of the zinc finger helix would not normally be positioned to bridge a base-pair step according to the Zif268 model, it is known that a bend in DNA can give scope to non-canonical zinc finger-DNA interactions ( L. Fairall, J. W. R. Schwabe, L. Chapman, J. T. Finch, D. Rhodes, (1993) *Nature* 366, 483–487). The sequence GGC (codon 10) is frequently found on the outside of a bend in the nucleosome core, and has been observed to confer an intrinsic bend in the crystal structure of a decameric DNA oligonucleotide. In the latter case, the bend arises from preferential stacking of the purines: this is associated with a large propeller twist and narrowing of the major groove, both of which would favour bridging of the base-pair step by asparagine ( T. E. Ellenberger, C. J. Brandl, K. Struhl, S. C. Harrison, (1992) Cell 71, 1223–1237). Therefore, in addition to explaining the selection of the non-canonical contact in the optimised complex, the sequence-dependent deformation of ras DNA could account for the observation that wild-type and EJ ras gene fragments have different electrophoretic mobility in polyacrylamide gets, since the wild-type ras gene has two GGC sequences 5 bp apart and hence out of helical phase (resulting in no net bend), while the EJ mutation affects one of these GGC sequences.

Thus, while it is possible to engineer an adequate DNA-binding domain by rational design based on recognition rules, the binding affinity of this lead peptide is improved using phase display leading to the selection of a non-canonical DNA contact.

EXAMPLE 5

Diagnosis of a ras Mutation Using the Zinc Finger Nucleic Acid Binding Protein

The optimised DNA-binding domain displayed on phage is applied in the diagnosis of the activating point mutation of the EJ ras oncogene. Bacterial culture supernatant containing the diagnostic phage is diluted 1:1 with PBS containing 50 μM $ZnCl_2$, 4% (w/v) fat-free dried milk (Marvel) and 2% (v/v) Tween-20. Biotinylated oligonucleotides (7.5 pmol) containing double stranded DNA comprising codons 8–16 from the wild type or the point-mutated ras gene are added to 50 μl of the diluted phage and incubated for Ih at 20° C. In the experiment shown in FIG. 8, bound phage are captured with 0.5 mg streptavidin coated paramagnetic beads (Dynal)—however streptavidin coated microtitre plates (Boehringer Mannheim) can also be used without alteration to the protocol. Unbound phage are removed by washing the beads 6 times with PBS containing 50 μM $ZnCl_2$ and 1% (v/v) Tween-20. The beads are subsequently incubated for 1 h at RT with anti-M13 IgG conjugated to horseradish peroxidase (PharmaciaBiotech) diluted 1:5000 in PBS containing 50 μM $ZnCl_2$ and 2% (w/v) fat-free dried milk (Marvel). Excess antibody is removed by washing 6 times with PBS containing 50 μM $ZnCl_2$ and 0.05% (v/v) Tween, and 3 times with PBS containing 50 μM $ZnCl_2$. The ELISA is developed with 0.1 mg/ml tetramethylbenzidine (Sigma) in 0.1M sodium acetate pH5.4 containing 2 μl of fresh 30% hydrogen peroxide per 10 ml buffer, and after approximately 1 min, stopped with an equal volume of 2M $H_2SO_4$. The reaction produces a yellow colour which is quantitated by subtracting the absorbance at 650 nm from the absorbance at 450 nm. It should be noted that in this protocol the ELISA is not made competitive, however, soluble (non biotinylated) wild-type ras DNA could be included in the binding reactions, possibly leading to higher discrimination between wild-type and mutant ras.

Figure 8:
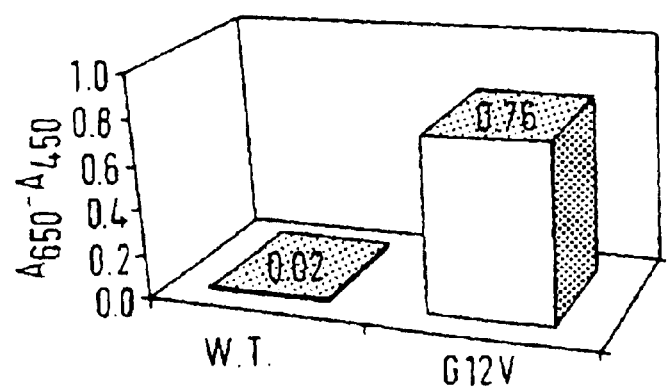
FIG. 8 illustrates the results of an ELISA assay performed using the anti-ras binding protein with both wild-type and mutant target nucleic acid sequences.

Phage are retained specifically b) DNA bearing the mutant, but not the wild-type ras sequence, allowing the detection of the point mutation by ELISA (FIG. 8).

EXAMPLE 6

Design of an Anti-HIV Zinc Ringer

The sequence of the HIV TAR, the region of the LTR which is responsible for trans-activation by Tat, is known (Jones and Peterlin, (1994) Ann. Rev. Biochem. 63;717–743). A sequence with the TAT region is identified and a zinc finger polypeptide designed to bind thereto.

The selected sequence is 5'-AGA GAG CTC-3' (SEQ ID NO: 13), which is the complement of nucleotides +34 to +42 of HIV. The corresponding amino acids required in fingers 1, 2 and 3 of a zinc finger binding protein are determined according to the rules set forth above, as follows:

| | | |
|---|---|---|
| Finger 3: | target | 5'-GAGA-3' |
| | Position −1 | Gln |
| | Position +2 | Gly |
| | Position +3 | His |
| | Position +6 | Val |
| Finger 2: | target | 5'-CGAG-3' |
| | Position −1 | Arg |
| | Position +2 | Ser |
| | Position +3 | Asn |
| | Position +6 | Arg |
| Finger 1: | target | 5'-CTC-3' |
| | Position −1 | Asp |
| | Position +3 | Ser |
| | Position +6 | Glu |

The framework of the polypeptide is taken from the Zif 268 middle finger. The sequence of the entire polypeptide is shown in SEQ. ID. No. 2.

Residues +2 and +6 of finger 3 are partially selected by randomisation and phage display selection. At position 2, two triplets are used, GAT and GGT, coding for Asp or Gly. Position +6 was randomised. In these positions, the residues Gly and Val are selected. The methodology employed is as follows: colony PCR is performed with one primer containing a single mismatch to create the required randomisations in finger 3. Cloning of PCR product in phage vector is as described previously (Choo, Y. & Klug, A. (1994) Proc. Natl. Acad. Sci. USA 91, 11163–11167; Choo, Y. & Klug, A. (1994) Proc. Natl. Acad. Sci. USA 91, 11168–11172). Briefly, forward and backward PCR primers contained unique restriction sites for Not I or Sfi I respectively and amplified an approximately 300 base pair region encompassing three zinc fingers. PCR products are digested with Sfi I and Not I to create cohesive ends and are ligated to 100 ng of similarly digested fd-Tet-SN vector. Electrocompetent TG1 cells are transformed with the recombinant vector. Single colonies of transformants are grown overnight in 2xTY containing 50 μM $ZnCl_2$ 15 μg/ml tetracycline. Single stranded DNA is prepared from phage in the culture supernatant and sequenced with Sequenase 2.0 (United States Biochemical).

The polypeptide designed according to the invention is then tested for binding to HIV DNA and positive results are obtained.

EXAMPLE 6

Design of a Zinc Finger Specific for an 8 bp Palindrome

Arrays of zinc fingers bind to asymmnetric DNA sequences but are not known to bind palindromes. In order to determine whether an array of zinc fingers can bind to a palindrome a three finger domain is engineered to recognise the 8 bp palindromic sequence GCGGCCGC (SEQ ID NO: 14) which is bound and cleaved by the restriction endonuclease NotI.

A zinc finger domain is selected from the a Zif268 middle finger library (see WO 96/06166) to bind the middle triplet GCC in the context of the Zif268 binding site. The sequence bound by this domain is GCG-GCC-GCG (SEQ ID NO:15).

In order to do change the specificity of the zinc finger to the NotI recognition sequence GCG-GCC-GC (SEQ ID NO: 16) the N-terminus of the α-helix of finger 1 (F1) is mutated from position −2 through to +2. Position −2 is Ser in WT Zif268 and could make a water mediated H-bond to a DNA phosphate: this is mutated to Arg in order to make a direct phosphate contact. Positions −1, 1 and 2 are mutated to Gly or Ala (Gly for −1 which is just outside the helix, and Ala for the other positions on the helix) in order to eliminate H-bonding groups which might function in DNA recognition. The protein is able to accept any base (N) in the sequence GCG-GCC-GCN with a small preference for A over G/T/C. The binding strength is not affected, even though the Arg->G contact of WT Zif268 is deleted, owing to compensation from the engineered phosphate contact. Thus a protein that bound the Bbp palindromic recognition site of NotI is engineered from a three finger domain based on Zif268.

The zinc finger domain selected from the library originally had Ser at position +3 of F2 and recognises the sequence GCGGYC-GCG (SEQ ID NO:17) where Y is C or T. Since recognition of the NotI site requires specifying C at that DNA position, the mutation Ser->Asp is made at position +3 of F2 to narrow the DNA binding specificity from Y to C. This mutation is according to the rules set forth above. The final construct binds the sequence GCG-GCC-GC specifically.

What is claimed is:

1. A method for preparing a nucleic acid binding protein that binds to a target nucleotide sequence, wherein the binding protein comprises a plurality of zinc fingers of the Cys2-His2 class, further wherein adjacent zinc fingers bind synergistically to overlapping quadruplet target subsites, wherein the method comprises:
   i) selecting a quadruplet within the target nucleotide sequence;
   ii) designing the binding protein such that binding of a zinc finger to the quadruplet is obtained by choosing the sequence of particular residues of the zinc finger depending on the nucleotide sequence of the quadruplet, as follows:
      a) if base 4 in the quadruplet is A, then position +6 in the α-helix is Glu, Asn or Val;
      b) if base 4 in the quadruplet is C, then position +6 in the α-helix is Ser, Thr, Val, Ala, Glu or Asn
      c) if base 4 in the quadruplet is G, then position +6 in the α-helix is Arg or Lys;
      d) if base 4 in the quadruplet is T, then position +6 in the α-helix is Ser, Thr, Val or Lys;
   iii) synthesizing a polynucleotide encoding the binding protein of (ii);
   iv) introducing the polynucleotide of (iii) into a cell; and
   v) incubating the cell under conditions in which the encoded nucleic acid binding protein is expressed.

2. A method according to claim 1, wherein base 4 is G or T.

3. A method for preparing a nucleic acid binding protein that binds to a target nucleotide sequence, wherein the binding protein comprises a plurality of zinc fingers of the Cys2-His2 class, wherein the method comprises:
   i) selecting a quadruplet within the target nucleotide sequence;
   ii) designing the binding protein such that binding of a zinc finger to the quadruplet is obtained by choosing the sequence of particular residues of the zinc finger depending on the nucleotide sequence of the quadruplet, as follows:

a) if base 4 in the quadruplet is G, then position +6 in the α-helix is Arg or Lys;
b) if base 4 in the quadruplet is A, then position +6 in the α-helix is Glu, Asn or Val;
c) if base 4 in the quadruplet is T, then position +6 in the α-helix is Ser, Thr, Val or Lys;
d) if base 4 in the quadruplet is C, then position +6 in the α-helix is Ser, Thr, Val, Ala, Glu or Asn;
e) if base 3 in the quadruplet is G, then position +3 in the α-helix is His;
f) if base 3 in the quadruplet is A, then position +3 in the α-helix is Asn;
g) if base 3 in the quadruplet is T, then position +3 in the α-helix is Ala, Ser or Val;
h) if base 3 in the quadruplet is C, then position +3 in the α-helix is Ser, Asp, Glu, Leu, Thr or Val;
i) if base 2 in the quadruplet is G, then position −1 in the α-helix is Arg;
j) if base 2 in the quadruplet is A, then position −1 in the α-helix is Gln;
k) if base 2 in the quadruplet is T, then position −1 in the α-helix is His or Thr;
l) if base 2 in the quadruplet is C, then position −1 in the α-helix is Asp or His;
m) if base 1 in the quadruplet is G, then position +2 is Glu;
n) if base 1 in the quadruplet is A, then position +2 Arg or Gln;
o) if base 1 in the quadruplet is C, then position +2 is Asn, Gln, Arg, His or Lys;
p) if base 1 in the quadruplet is T, then position +2 is Ser or Thr iii) synthesizing a polynucleotide encoding the binding protein of (ii);
iv) introducing the polynucleotide of (iii) into a cell; and
v) incubating the cell under conditions in which the encoded nucleic acid binding protein is expressed.

4. A method according to claim 3, wherein the each zinc finger has the general primary structure

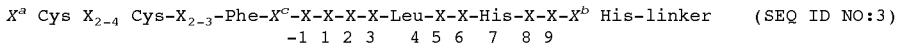

wherein X (including $X^a$, $X^b$ and $X^c$) is any amino acid.

5. A method according to claim 4 wherein Xa is Phe/Tyr-X or Pro-Phe/Tyr-X.

6. A method according to claim 5 wherein $X_{2-4}$ is selected from any one of:
Ser-X, Glu-X, Lys-X, Thr-X, Pro-X and Arg-X.

7. A method according to claim 4 wherein $X^b$ is Thr or Ile.

8. A method according to claim 4 wherein $X^{2-4}$ is Gly-Lys-Ala, Gly-Lys-Cys, Gly-Lys-Ser, Gly-Lys-Gly, Met-Arg-Asn or Met-Arg.

9. A method according to claim 4 wherein the linker is Thr-Gly-Glu-Lys (SEQ ID NO: 4) or Thr-Gly-Glu-Lys-Pro (SEQ ID NO: 5).

10. A method according to claim 4 wherein position +9 is Arg or Lys.

11. A method according to claim 4 wherein positions +1, +5 and +8 are not occupied by any one of the hydrophobic amino acids, Phe, Trp or Tyr.

12. A method according to claim 11 wherein positions +1, +5 and +8 are occupied by the residues Lys, Thr and Gln respectively.

13. A method for preparing a nucleic acid binding protein of the Cys2-His2 zinc finger class which binds a target nucleic acid sequence, comprising the steps of:
a) selecting a model zinc finger domain from the group consisting of naturally occurring zinc fingers and consensus zinc fingers; and
b) mutating the finger according to the rules set in any one of claims 1 to 3.

14. A method according to claim 13, wherein the model zinc finger is a consensus zinc finger whose structure is selected from the group consisting of the consensus structure Pro-Tyr-Lys-Cys-Pro-Glu-Cys-Gly-Lys-Ser-Phe-Ser-Gln-Lys-Ser-Asp-Leu-Val-Lys-His-Gln-Arg-Thr-His-Thr-Gly (SEQ ID NO: 6), and the consensus structure Pro-Tyr-Lys-Cys-Ser-Glu-Cys-Gly-Lys-Ala-Phe-Ser-Gln-Lys-Ser-Asn-Leu-Thr-Arg-His-Gln-Arg-Ile-His-Thr-Gly-Glu-Lys-Pro (SEQ ID NO: 7).

15. A method according to claim 13 wherein the model zinc finger is a naturally-occurring zinc finger whose structure is selected from one finger of a protein selected from the group consisting of Zif 268, GLI, Tramtrack and YY1.

16. A method according to claim 15 wherein the model zinc finger is finger 2 of Zif 268.

17. A method according to claim 3 wherein the binding protein comprises two or more zinc finger binding motifs, placed N-terminus to C-terminus.

18. A method according to claim 14, wherein the N-terminal zinc finger is preceded by a leader peptide having the sequence Met-Ala-Glu-Glu-Lys-Pro (SEQ ID NO: 8).

19. A method according to claim 13 wherein the nucleic acid binding protein is obtained by recombinant nucleic acid technology, the method comprising the steps of:
a) preparing a nucleic acid coding sequence encoding two or more model zinc finger domains, placed N-terminus to C-terminus;
b) inserting the nucleic acid sequence into a suitable expression vector; and
c) expressing the nucleic acid sequence in a host organism in order to obtain the nucleic acid binding protein.

20. A method according to claim 3 comprising the additional steps of subjecting the nucleic acid binding protein to one or more rounds of randomisation and selection in order to improve the characteristics thereof.

21. A method according to claim 20, wherein the randomisation and selection is carried out by phage display technology.

22. A method according to claim 21, comprising the steps of:
a) preparing a nucleic acid construct which express a fusion protein comprising the nucleic acid binding protein and a minor coat protein of a filamentous bacteriophage;
b) preparing further nucleic acid constructs which express a fusion protein comprising a selectively mutated nucleic acid binding protein and a minor coat protein of a filamentous bacteriophage;
c) causing the fusion proteins defined in steps (a) and (b) to be expressed on the surface of bacteriophage transformed with the nucleic acid constructs;
d) assaying the ability of the bacteriophage to bind the target nucleic acid sequence and selecting the bacteriophage demonstrating superior binding characteristics.

23. A method according to claim 20 wherein the nucleic acid binding protein is selectively randomised at any one of positions +1, +5, +8, −1, +2, +3 or +6.

24. A method according to claim 23, wherein, in the nucleic acid binding protein, position +6 of a zinc finger and positions −1, +1, +2 and +3 of an adjacent zinc finger are randomised.

25. The method of claim 3, wherein a plurality of overlapping quadruplets are selected within the target sequence.

* * * * *

SEQUENCE LISTING

<160> NUMBER OF SEQ ID NOS: 114

<210> SEQ ID NO 1
<211> LENGTH: 264
<212> TYPE: DNA
<213> ORGANISM: Artificial Sequence
<220> FEATURE:
<221> NAME/KEY: CDS
<222> LOCATION: (1)..(264)
<223> OTHER INFORMATION: Description of Artificial Sequence: Synthetic
      DNA

<400> SEQUENCE: 1

```
gca gaa gag aag cct ttt cag tgt cga atc tgc atg cgt aac ttc agc      48
Ala Glu Glu Lys Pro Phe Gln Cys Arg Ile Cys Met Arg Asn Phe Ser
 1               5                  10                  15 gat cgt act act ctt acc cgc cac acg agg acc cac aca ggc gag aag      96
Asp Arg Thr Thr Leu Thr Arg His Thr Arg Thr His Thr Gly Glu Lys
             20                  25                  30 cct ttt cag tgt cga atc tgc atg cgt aac ttc agc agg agc gat aac     144
Pro Phe Gln Cys Arg Ile Cys Met Arg Asn Phe Ser Arg Ser Asp Asn
         35                  40                  45 ctt acg aga cac cta agg acc cac aca ggc gag aag cct ttt cag tgt     192
Leu Thr Arg His Leu Arg Thr His Thr Gly Glu Lys Pro Phe Gln Cys
     50                  55                  60 cga atc tgc atg cgt aac ttc agg caa gct gat cat ctt caa gag cac     240
Arg Ile Cys Met Arg Asn Phe Arg Gln Ala Asp His Leu Gln Glu His
 65                  70                  75                  80 cta aag acc cac aca ggc gag aag                                     264
Leu Lys Thr His Thr Gly Glu Lys
                 85
```

<210> SEQ ID NO 2
<211> LENGTH: 88
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 2

```
Ala Glu Glu Lys Pro Phe Gln Cys Arg Ile Cys Met Arg Asn Phe Ser
 1               5                  10                  15

Asp Arg Thr Thr Leu Thr Arg His Thr Arg Thr His Thr Gly Glu Lys
             20                  25                  30

Pro Phe Gln Cys Arg Ile Cys Met Arg Asn Phe Ser Arg Ser Asp Asn
```

```
                35                  40                  45
Leu Thr Arg His Leu Arg Thr His Thr Gly Glu Lys Pro Phe Gln Cys
     50                  55                  60
Arg Ile Cys Met Arg Asn Phe Arg Gln Ala Asp His Leu Gln Glu His
 65                  70                  75                  80
Leu Lys Thr His Thr Gly Glu Lys
                 85

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Zinc finger
      motif
<221> NAME/KEY: MOD_RES
<222> LOCATION: (1)
<223> OTHER INFORMATION: Any amino acid
<221> NAME/KEY: MOD_RES
<222> LOCATION: (3)..(6)
<223> OTHER INFORMATION: This region may encompass 2-4 residues
      consisting of any amino acid
<221> NAME/KEY: MOD_RES
<222> LOCATION: (8)..(10)
<223> OTHER INFORMATION: This region may encompass 2-3 residues
      consisting of any amino acid
<221> NAME/KEY: MOD_RES
<222> LOCATION: (12)..(16)
<223> OTHER INFORMATION: Any amino acid
<221> NAME/KEY: MOD_RES
<222> LOCATION: (18)..(19)
<223> OTHER INFORMATION: Any amino acid
<221> NAME/KEY: MOD_RES
<222> LOCATION: (21)..(23)
<223> OTHER INFORMATION: Any amino acid

<400> SEQUENCE: 3

Xaa Cys Xaa Xaa Xaa Xaa Cys Xaa Xaa Xaa Phe Xaa Xaa Xaa Xaa Xaa
 1               5                  10                  15
Leu Xaa Xaa His Xaa Xaa Xaa His
             20

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Linker

<400> SEQUENCE: 4

Thr Gly Glu Lys
 1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Linker

<400> SEQUENCE: 5

Thr Gly Glu Lys Pro
 1               5

<210> SEQ ID NO 6
<211> LENGTH: 26
<212> TYPE: PRT
<213> ORGANISM: Artificial Sequence
```

```
<220> FEATURE:
<223> OTHER INFORMATION: Description of Artificial Sequence: Consensus
      structure

<400> SEQUENCE: 6

Pro Tyr Lys Cys Pro Glu Cys Gly Lys Ser Phe Ser Gln Lys Ser Asp
 1               5                  10                  15

Leu Val Lys His Gln Arg Thr His Thr Gly
            20                  25

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Consensus
      structure

<400> SEQUENCE: 7

Pro Tyr Lys Cys Ser Glu Cys Gly Lys Ala Phe Ser Gln Lys Ser Asn
 1               5                  10                  15

Leu Thr Arg His Gln Arg Ile His Thr Gly Glu Lys Pro
            20                  25

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Leader
      peptide

<400> SEQUENCE: 8

Met Ala Glu Glu Lys Pro
 1               5

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 9

Phe Gln Cys Arg Ile Cys Met Arg Asn Phe Ser Asp Arg Ser Ser Leu
 1               5                  10                  15

Thr Arg His Thr Arg Thr His Thr Gly Glu Lys Pro
            20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 10

Phe Gln Cys Arg Ile Cys Met Arg Asn Phe Ser Asp Arg Ser His Leu
 1               5                  10                  15

Thr Arg His Thr Arg Thr His Thr Gly Glu Lys Pro
            20                  25

<210> SEQ ID NO 11
```

```
<211> LENGTH: 27
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 11

Phe Gln Cys Arg Ile Cys Met Arg Asn Phe Ser Asp Arg Ser Asn Leu
 1               5                  10                  15

Thr Arg His Thr Arg Thr His Thr Gly Glu Lys
            20                  25

<210> SEQ ID NO 12
<211> LENGTH: 36
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 12

Met Ala Glu Glu Arg Pro Tyr Ala Cys Pro Val Glu Ser Cys Asp Arg
 1               5                  10                  15

Arg Phe Ser Arg Ser Asp Glu Leu Thr Arg His Ile Arg Ile His Thr
            20                  25                  30

Gly Gln Lys Pro
        35

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 13

Phe Gln Cys Arg Ile Cys Met Arg Asn Phe Ser Arg Ser Asp Asp Leu
 1               5                  10                  15

Thr His Ile Arg Thr His Thr Gly Glu Lys Pro
            20                  25

<210> SEQ ID NO 14
<211> LENGTH: 26
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 14

Phe Ala Cys Asp Ile Cys Gly Arg Lys Phe Ala Ser Asp Arg Lys Arg
 1               5                  10                  15

His Thr Lys Ile His Leu Arg Gln Lys Asp
            20                  25

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 15
```

Arg Leu Glu Tyr
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 16

Arg Ser Glu Asp
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 17

Arg His Thr His
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 18

Arg Ser Ser Glu
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 19

Arg Ser Ser Ala
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 20

Gln Val Thr Thr
1

<210> SEQ ID NO 21
<211> LENGTH: 4
<212> TYPE: PRT
<213> ORGANISM: Artificial Sequence

```
<220> FEATURE:
<223> OTHER INFORMATION: Description of Artificial Sequence: Zinc finger
      peptide

<400> SEQUENCE: 21

Gln Ser Gly Asp
  1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 22

Gln Leu Ala Thr
  1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 23

Gln Asp Ala His
  1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 24

Gln Arg Ala Ser
  1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 25

Gln Ser Thr Ser
  1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 26

Ser Ser Gly Asp
  1
```

-continued

```
<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 27

Ser Ala Ser Ala
  1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 28

Asn Ser Gly Asp
  1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 29

Leu Val Gln Asn
  1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 30

Thr Gly Ala Ser
  1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 31

Thr Pro Ser Gly
  1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide
```

```
<400> SEQUENCE: 32

Thr Gln Thr Ala
 1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 33

Thr Ser Ala Ala
 1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 34

Asp Thr Ser Val
 1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 35

Asp Ala Ser Thr
 1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 36

Asp Ala Ser Ala
 1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 37

Asp Thr Ser Ser
 1

<210> SEQ ID NO 38
<211> LENGTH: 4
<212> TYPE: PRT
```

```
<213> ORGANISM: Artificial Sequence
<220> FEATURE:
<223> OTHER INFORMATION: Description of Artificial Sequence: Zinc finger
      peptide

<400> SEQUENCE: 38

Arg Asn His Asp
  1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 39

Arg Ser Thr Asp
  1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 40

Arg Ser Thr Asp
  1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 41

Ser Arg His Ser
  1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 42

Arg Asn Ser Thr
  1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 43

Arg Thr Ser Thr
  1
```

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 44

Thr Arg Tyr Ser
 1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 45

Arg Ala Gln Asn
 1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 46

Gln Ala Ala Thr
 1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 47

Gln Gly Thr Asn
 1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 48

Thr Ser Arg Asp
 1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

```
<400> SEQUENCE: 49

Gln Arg Gly Ala
 1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 50

Gln Ser Thr Thr
 1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 51

Thr Ser Ser Ser
 1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 52

Ser Ser Ser Thr
 1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 53

Thr Ile Ser Asn
 1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 54

Thr Ser Thr Ala
 1

<210> SEQ ID NO 55
<211> LENGTH: 4
```

```
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 55

Thr Ser Ser Leu
  1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 56

Thr Ser Ser Ile
  1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 57

Thr Ser Asn Ser
  1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 58

Gly Ser Asn Asp
  1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 59

Thr Thr Ser Ser
  1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 60

Thr Ala Gly Ser
```

```
<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 61

Thr Thr Ser Ser
 1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 62

Thr Ser Ser Ala
 1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 63

Leu Ser Thr Thr
 1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 64

Leu Ser Ser Thr
 1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 65

Asp Pro His Asn
 1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Zinc finger
``` peptide

<400> SEQUENCE: 66

His Ser Lys Ser
1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 67

His Arg Gln Asn
1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 68

Asp Arg Ala Asn
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 69

Asp Arg Ala Asn
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 70

Arg Ser Gln Asp
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 71

Gln Val Gly His
1

<210> SEQ ID NO 72

```
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 72

Gln Leu Ala Thr
 1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 73

Thr Ser Gln Ala
 1

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 74

Thr Ser Ala Ser
 1

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 75

Leu Ala Gln Thr
 1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 76

Arg Ser Arg Asp
 1

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 77
```

Arg Leu Arg Asp
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 78

His Leu Ala Thr
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 79

His Leu Thr Thr
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 80

Val Gly His His
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 81

His Pro Ala Thr
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 82

His Pro Ala Asn
1

<210> SEQ ID NO 83
<211> LENGTH: 4
<212> TYPE: PRT
<213> ORGANISM: Artificial Sequence
<220> FEATURE:

```
<223> OTHER INFORMATION: Description of Artificial Sequence: Zinc finger
      peptide

<400> SEQUENCE: 83

His His Ser Asn
 1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 84

Asp Ser Arg Ala
 1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 85

Lys Ser Ser Asp
 1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 86

Ser Ser Ser Asp
 1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 87

Arg Ser His Asp
 1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 88

Arg Ser Ser Tyr
 1
```

```
<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 89

Arg Ser Ser Ser
 1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 90

Arg Lys Thr Asp
 1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 91

Gln Ile Ser Thr
 1

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 92

Gln Ile Gly Ala
 1

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 93

Gln Tyr Ser Thr
 1

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 94
```

-continued

Gln Ser Ala Ser
1

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 95

Gln Ser Gln His
1

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 96

Gln Thr Ser His
1

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 97

Gln Pro Gly His
1

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 98

Gln Asp Thr Thr
1

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 99

Gln Asp Ser Thr
1

<210> SEQ ID NO 100
<211> LENGTH: 4
<212> TYPE: PRT
<213> ORGANISM: Artificial Sequence

```
<220> FEATURE:
<223> OTHER INFORMATION: Description of Artificial Sequence: Zinc finger
      peptide

<400> SEQUENCE: 100

Thr Ala Ser Thr
 1

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 101

Thr Ala Ser His
 1

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 102

Thr Ser Ser Val
 1

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 103

Thr Ser Ser Ala
 1

<210> SEQ ID NO 104
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 104

His His Thr Ser
 1

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 105

His Ala Gln Thr
 1
```

```
<210> SEQ ID NO 106
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 106

His Ala Thr Thr
  1

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 107

Asp His Ser Ser
  1

<210> SEQ ID NO 108
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 108

His Pro Ser Thr
  1

<210> SEQ ID NO 109
<211> LENGTH: 4
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 109

Asp Ser Ser Arg
  1

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 110
gtggtgggcg ccggcggtgt gggcaag                                    27

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 111
```

```
gtggtgggcg ccgtcggtgt gggcaag                                              27
```

```
<210> SEQ ID NO 112
<211> LENGTH: 34
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 112

Met Ala Glu Glu Lys Pro Phe Gln Cys Arg Ile Cys Met Arg Asn Phe
1               5                   10                  15

Ser Asp Arg Ser Ser Leu Thr Arg His Thr Arg Thr His Thr Gly Glu
            20                  25                  30

Lys Pro

<210> SEQ ID NO 113
<211> LENGTH: 28
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 113

Phe Gln Cys Arg Ile Cys Met Arg Asn Phe Ser Asp Arg Ser Ser Leu
1               5                   10                  15

Thr Arg His Thr Arg Thr His Thr Gly Glu Lys Pro
            20                  25

<210> SEQ ID NO 114
<211> LENGTH: 27
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 114

Phe Gln Cys Arg Ile Cys Met Arg Asn Phe Ser Asp Arg Ser Ser Leu
1               5                   10                  15

Thr Arg His Thr Arg Thr His Thr Gly Glu Lys
            20                  25
```